United States Patent [19]
Williamson

[11] Patent Number: 6,111,092
[45] Date of Patent: Aug. 29, 2000

[54] NUCLEIC ACID MOLECULES ENCODING DRT111 AND USES THEREOF

[75] Inventor: Mark Williamson, Saugus, Mass.

[73] Assignee: Millennium Pharmaceuticals, Inc., Cambridge, Mass.

[21] Appl. No.: 09/089,879

[22] Filed: Jun. 3, 1998

[51] Int. Cl.[7] .......................... C07H 21/04; C12N 15/11; C12N 15/00; C12N 15/85; C12Q 1/68
[52] U.S. Cl. .................... 536/23.5; 536/23.1; 536/24.31; 435/6; 435/69.1; 435/325; 435/352; 435/354
[58] Field of Search ............................... 435/6, 69.1, 91.1, 435/440, 455, 352, 325, 366, 375, 354, 243, 320.1; 536/23.1, 23.5, 24.3, 24.31, 24.33; 514/44

[56] References Cited

PUBLICATIONS

Barret et al., "DNA Repair Mechanisms Associated With Cellular Resistance to Antitumor Drugs: Potential Novel Targets", Anti–Cancer Drugs 9:105–123, 1998.

Belanich et al., "Retrospective Study of the Correlation Between the DNA Repair Protein Alkyltransferase and Survival of Brain Tumor Patients Treated with Carmustine", Cancer Research 56:783–788, 1996.

Fink et al., "The Effect of Different Chemotherapeutic Agents on the Enrichment of DNA Mismatch Repair–Deficient Tumour Cells", British Journal of Cancer 77:703–708, 1998.

Friedman et al., "Elevated DNA Polymerase α, DNA Polymerase β, and DNA Topoisomerase II in a Melphalan–Resistant Rhabdomyosarcoma Xenograft that Is Cross–Resistant to . . . " Cancer Research 54:3487–3493, 1994.

Ludlum, "The Chloroethylnitrosoureas: Sensitivity and Resistance to Cancer Chemotherapy at the Molecular Level", Cancer Investigation 15:588–598, 1997.

Pang et al., "Two cDNAa From The Plant *Arabidopsis Thaliana* That Partially Restore Recombination Proficiency and DNA–Damage Resistance to *E. Coli* Mutants Lacking . . . " Nucleic Acids Res. 21:1647–1653, 1993.

Teicher et al., "Tumor Resistance to Alkylating Agents Conferred by Mechanisms Operative Only In Vivo", Science 24:1457–1461, 1990.

*Primary Examiner*—David Guzo
*Assistant Examiner*—Mark L. Shibuya
*Attorney, Agent, or Firm*—Fish & Richardson, P.C.

[57] ABSTRACT

Novel DRT111 polypeptides, proteins, and nucleic acid molecules are disclosed. In addition to an isolated, full-length DRT111 protein, the invention further provides isolated DRT111 fusion proteins, antigenic peptides and anti-DRT111 antibodies. The invention also provides DRT111 nucleic acid molecules, recombinant expression vectors containing a nucleic acid molecule of the invention, host cells into which the expression vectors have been introduced and non-human transgenic animals in which a DRT111 gene has been introduced or disrupted. Diagnostic, screening and therapeutic methods utilizing compositions of the invention are also provided.

6 Claims, 5 Drawing Sheets

Human DRT111 Clone

```
GTCGACCCACGCGTCCGGGGTGGGCGCCGCCGAGGCCTCCTGCCGCTGGCGGGTTTCCGCGGAGTGCCGCCCGGCTCCGC
TCTGCCGCCGGCGCGGCTCATGGGCAGAGTCGGCCGGGCGGGCCGGCATTAAACTGAAGAAAAGATGTCCCTGTACGATG
ACCTAGGAGTGGAGACCAGTGACTCAAAAACAGAAGGCTGGTCCAAAAACTTCAAACTTCTGCAGTCTCAGCTTCAGGTG
AAGAAGGCAGCTCTCACTCAGGCAAAGAGCCAAAGGACGAAACAAAGTACAGTCCTCGCCCCAGTCATTGACCTGAAGCG
AGGTGGCTCCTCAGATGACCGGCAAATTGTGGACACTCCACCGCATGTAGCAGCTGGGCTGAAGGATCCTGTTCCCAGTG
GGTTTTCTGCAGGGGAAGTTCTGATTCCCTTAGCTGACGAATATGACCCTATGTTTCCTAATGATTATGAGAAAGTAGTG
AAGCGCCAAAGAGAGGAACGACAGAGACAGCGGGAGCTGGAAAGACAAAAGGAAATAGAAGAAAGGGAAAAAAGGCGTAA
AGACAGACATGAAGCAAGTGGGTTTGCAAGGAGACCAGATCCAGATTCTGATGAAGATGAAGATTATGAGCGAGAGAGGA
GGAAAAGAAGTATGGGCGGAGCTGCCATTGCCCCACCCACTTCTCTGGTAGAGAAAGACAAAGAGTTACCCCGAGATTTT
CCTTATGAAGAGGACTCAAGACCTCGATCACAGTCTTCCAAAGCAGCCATTCCTCCCCAGTGTACGAGGAACAAGACAG
ACCGAGATCTCCAACCGGACCTAGCAACTCCTTCCTCGCTAACATGGGGGCACGGTGGCGCACAAGATCATGCAGAAGT
ACGGCTTCCGGGAGGGCCAGGGTCTGGGGAAGCATGAGCAGGGCCTGAGCACTGCCTTGTCAGTGGAGAAGACCAGCAAG
CGTGGCGGCAAGATCATCGTGGGCGACGCCACAGAGAAAGATGCATCCAAGAAGTCAGATTCAAAATCCGCTGACTGAAA
TACTTAAGTGTCCTACTAAAGTGGTCTTACTAAGGAACATGGTTGGTGCGGGAGAGGTGGATGAAGACTTGGAAGTTGAA
ACCAAGGAAGAATGTGAAAAATATGGCAAAGTTGGAAAATGTGTGATATTTGAAATTCCTGGTGCCCCTGATGATGAAGC
AGTACGGATATTTTTAGAATTTGAGAGAGTTGAATCAGCAATTAAAGCGGTTGTTGACTTGAATGGGAGGTATTTTGGTG
GACGGGTGGTAAAAGCATGTTTCTACAATTTGGACAAATTCAGGGTCTTGGATTTGGCAGAACAAGTTTGATTTAAGAA
CTAGAGCACGAGTCATCTCCGGTGATCCTTAAATGAACTGCAGGCTGAGAAAAGAAGGAAAAAGGTCACAGCCTCCATGG
CTGTTGCATACCAAGACTCTTGGAAGGACTTCTAAGATATATGTTGATTGATCCCTTTTTTATTTTGTGGTTTTTTAATA
TAGTATAAAAATCCTTTTAAAAAAACAACAATCTGTGTGCCTCTCTGGTTGTTTCTCTTTTTTATTATTACTCCTGAGTT
GATGACATTTTTTGTTAGATTTCATGGTAATTCTCAAGTGCTTCAATGATGCAGCATTTCTTGCACTAAAAAAAAAAAAA
AAAAAGGGCGGCCGC
```

SEQ ID NO:1

Amino Acid Sequence of Human DRT111:

```
MSLYDDLGVETSDSKTEGWSKNFKLLQSQLQVKKAALTQAKSQRTKQSTVLAPVIDLKRGGSSDDRQIVDTPPHVAAGLK
DPVPSGFSAGEVLIPLADEYDPMFPNDYEKVVKRQREERQRQRELERQKEIEEREKRRKDRHEASGFARRPDPDSDEDDY
ERERRKRSMGGAAIAPPTSLVEKDKELPRDFPYEEDSRPRSQSSKAAIPPPVYEEQDRPRSPTGPSNSFLANMGGTVAHK
IMQKYGFREGQGLGKHEQGLSTALSVEKTSKRGGKIIVGDATEKDASKKSDSNPLTEILKCPTKVVLLRNMVGAGEVDED
LEVETKEECEKYGKVGKCVIFEIPGAPDDEAVRIFLEFERVESAIKAVVDLNGRYFGGRVVKACFYNLDKFRVLDLAEQV
*
```

SEQ ID NO:2

```
                                                                                         Majority
    T G P S N S F L A N M G G T V A H K I M Q K Y G F R E G Q G L G K H E Q G L S T 203 T G V G A G - - G O M - - T P A Q R M M P K M G W K Q G Q G L G K S E Q G L P T      DRT111.PROT
224 T G P S N S F L A N M G G T V A H K I M Q K Y G F R E G Q G L G K H E Q G L S T      HDRT111PROTEIN
224 T G P S N S F L A N M G G T V A H K I M Q K Y G F R E G Q G L G K H E Q G L S T      mDRT111.pep Majority
    A L S V E K T S K R G G K I I V G D A T E X X X X A X D A S K K S D S N P L T E I 239 P L M A K I K T D R R A G V I V N A S E N K S S S A E K K Y V K S - - - - Y N I      DRT111.PROT
264 A L S V E K T S K R G G K I I V G D A T E K - - - D A S K K S D S N P L T E I        HDRT111PROTEIN
264 A L S V E K T S K R G G K I I V G D A T E X G E A Q D A S K K S D S N P L T E I      mDRT111.pep Majority
    L K C P T K V V L L R N M V G A G E V D E D - - - - L E V E T K E E C E K Y G 274 N G E P T R V L L F E I T E P N E P V H E A V R I F L E F E R V E S A I K A V V D L  DRT111.PROT
300 L K C P T K V V L L R N M V G P G Q V D D E - - - - L E V E T K E E C E K Y G        HDRT111PROTEIN
304 L K C P T K V V L L R N M V G A G E V D E D - - - - L E V E T K E E C E K Y G        mDRT111.pep Majority
    K V G K C V I F E I - - P G A P D D E A V R I F L E F E R V E S A I K A V V D L 309 T V T R V L I F E I T E P N E P V H E A V R I F V Q F S R P E E T T K A L V D L      DRT111.PROT
335 K V G K C V I F E I - - P G A P D D E A V R I F L E F E R V E S A I K A V V D L      HDRT111PROTEIN
339 K V G K C V I F E I - - P G A P D D E A V R I F L E F E R V E S A I K A V V D L      mDRT111.pep Majority
    N G R Y F G G R V V K A C F Y N L D K F R V L D L A X X X X X X X P X - - - - -

349 D G R Y F G G R T V R A T F Y D E E K F S K N E L A P V P G - - - E I E G Y          DRT111.PROT
373 N G R Y F G G R V V K A C F Y N L D K F R V L D L A E Q V                            HDRT111PROTEIN
377 N G X Y F G G R V V K A C F Y N L D K F R V L D L A D K F D C N L K S E P            mDRT111.pep
```

Decoration 'Decoration #1': Box residues that match the Consensus exactly.

Murine DRT111 Nucleic Acid Sequence

>mDRT111seq
CTACACCCCGCGTACGCGGACGCGTGGGGCGCTGCGGCGGACTCCGGCGGTGGGCGGGCT
TCCGCGCAGGGCGGCCGGGCTCCGCGCTGCCGCCGCCGTGGCCCATGGGCACAATCGTCT
CGGAAGGCCGGCATTAAACCAAAAAGATGTCCCTATATGATGACCTGGGAGTGGAGACCA
GTGACTCAAAAACTGAAGGCTGGTCCAAAAACTTCAAGCTCCTGCAGTCCCAGCTCCAGG
TGAAGAAGGCGGCGCTCACTCAGGCCAAGAGCCAAAGGACCAAGCAAAGTACAGTGCTTG
CTCCGGTCATCGACCTAAAGCGAGGCGGCTCCTCAGATGACCGGCAGATTGCAGACACAC
CACCTCACGTGGCAGCTGGGCTGAAGGACCCTGTGCCCAGTGGGTTTTCTGCAGGGGAAG
TTCTGATCCCCTTAGCTGATGAATATGACCCTATGTTCCCCAATGACTATGAGAAAGTGG
TGAAGCGCCAGAGAGAAGAGCGGCAGAGGCAGCGGGAGCTGGAAAGACAGAAGGAAATAG
AGGAAAGAGAAAAGAGGCGTAAAGACAGACACGAAGCCAGTGGGTTTTCAAGACGACCAG
ACCCTGATTCTGATGAGGATGAAGATTATGAGCGAGAGCGNNGGAAAAGAAGTATGGGAG
GAGCTGCCATCGCCCCACCGACGTCTCTTGTAGAGAAAGACAAAGAGTTACCCCGCGATT
TTCCTTATGAAGAGGACTCAAGACCGAGATCACAGTCTTCCAAAGCTGCTATTCCTCCCC
CCGTGTATGAGGAGCCGGACAGACCAAGATCTCCAACAGGCCCCAGCAACTCCTTCCTTG
CTAACATGGGTGGCACAGTGGCTCATAAGATTATGCAGAAGTATGGCTTCCGGGAAGGTC
AGGGACTGGGGAAACACGAGCAAGGGCTGAGTACTGCATTGTCTGTGGAGAAGACCAGCA
AGCGTGGCGGCAAGATCATTGTGGGGGATGCGACAGAGAANGGCGAGGCTCAGGATGCAT
CCAAAAAGTCGGATTCAAATCCATTAACTGAAATTCTTAAGTGCCCTACTAAAGTGGTCT
TGCTGAGGAACATGGTTGGTGCAGGAGAGGTCGATGAAGACTTGGAAGTTGAAACCAAGG
AAGAATGTGAAAAATATGGCAAAGTTGGGAAATGTGTGATATTTGAGATTCCTGGTGCCC
CTGATGATGAAGCAGTACGGATATTTTTAGAATTTGAGAGAGTCNAATCAGCAATTAAAG
CTGTGGTGGATCTGAATGGGANGTATTTTGGTGGACGGGTGGTAAAAGCATGTTTCTACA
ATTTGGATAAATTCAGGGTCTTGGATCTAGCAGACAAGTTTGATTGTAACTTAAAGTCAC
CTCCTTGATCCTTACATGAGCTACAGACTGAACAATGACACAGGCATGGCTGTTGTGTCA
TGGCTGGTGGACCTGAAACTCTTGGATGGCTTCTAAATATTGTTGAGGATCTTTTTTATA
TGTGGTTCTTATATAGATAAATCTTTAAATCAAAAAAAAAAA

SEQ ID NO:6

Murine DRT111 Amino Acid Sequence

>mDRT111
MSLYDDLGVETSDSKTEGWSKNFKLLQSQLQVKKAALTQAKSQRTKQSTVLAPVIDLKRGGSSDDRQIADTPPHVAAGLK
DPVPSGFSAGEVLIPLADEYDPMFPNDYEKVVKRQREERQRQRELERQKEIEEREKRRKDRHEASGFSRRPDPDSDEDED
YERERXKRSMGGAAIAPPTSLVEKDKELPRDFPYEEDSRPRSQSSKAAIPPPVYEEPDRPRSPTGPSNSFLANMGGTVAH
KIMQKYGFREGQGLGKHEQGLSTALSVEKTSKRGGKIIVGDATEXGEAQDASKKSDSNPLTEILKCPTKVVLLRNMVGAG
EVDEDLEVETKEECEKYGKVGKCVIFEIPGAPDDEAVRIFLEFERVXSAIKAVVDLNGXYFGGRVVKACFYNLDKFRVLD
LADKFDCNLKSPP

SEQ ID NO:7

FIG. 3

NUCLEIC ACID MOLECULES ENCODING DRT111 AND USES THEREOF

BACKGROUND OF THE INVENTION

The invention relates to chemotherapy and DNA repair.

Cancer chemotherapy involves the administration of one or more cytotoxic or cytostatic drugs to a patient. The goal of chemotherapy is to eradicate a substantially clonal population (tumor) of transformed cells from the body of the individual, or to suppress or to attenuate growth of the tumor. Tumors may occur in solid or liquid form, the latter comprising a cell suspension in blood or other body fluid. A secondary goal of chemotherapy is stabilization (clinical management) of the afflicted individual's health status. Although the tumor may initially respond to chemotherapy, in many instances the initial chemotherapeutic treatment regimen becomes less effective or ceases to impede tumor growth. The selection pressure induced by chemotherapy promotes the development of phenotypic changes that allow tumor cells to resist the cytotoxic effects of a chemotherapeutic drug.

Several chemotherapeutic drugs function by preferentially damaging DNA in actively dividing cells. The treated cells stop proliferating because the damaged genomic DNA is unable to support further mitosis. Types of DNA-damaging chemotherapeutic drugs include those that covalently modify bases (e.g., alkylating agents such as cyclophosphamide) and base analogs (e.g., 5-bromouracil). After chronic exposure to these drugs, tumor cells can become resistant to their effects.

One mechanism by which cells resist chemotherapeutic drugs is modulation of DNA repair processes. For an overview, see, Barrett et al. (1998) *Anticancer Drugs*, 9:105–123. The expression or activity of several different enzymes involved in repairing damaged DNA are altered in chemotherapeutic drug-resistant cells. For example, $O^6$-alkylguanine-DNA alkyltransferase, a DNA repair enzyme, exhibits higher expression in cells less sensitive to alkylating chemotherapeutic drugs than in cell more sensitive to the drugs. Belanich et al. (1996) *Cancer Res.*, 56:783–788. Similarly, DNA polymerase α, DNA polymerase β, and topoisomerase II are elevated in some tumor cells that are resistant to chemotherapeutic drugs. Friedman et al. (1994) *Cancer Res.*, 54:3487–93. In addition to these, many more DNA repair enzymes are aberrantly expressed in some drug-resistant tumor cells, including, for example: AP endonuclease and DNA glycosylases. See, Barrett et al., supra.

SUMMARY OF THE INVENTION

The present invention is based, at least in part, on the discovery of the human gene encoding DRT111. The apparent murine homolog of human DRT111 is expressed at a higher level in a cyclophosphamide-resistant variant of the murine tumor cell line EMT-6 CTX than in the EMT-6 cell line from which EMT-6 CTX tumor cells are derived. The human DRT111 cDNA described below (SEQ ID NO:1) has a 1203 nucleotide open reading frame (nucleotides 145–1348 of SEQ ID NO:1; SEQ ID NO:3) which encodes a 401 amino acid protein (SEQ ID NO:2). The cDNA encoding human DRT111 is 35% identical to the cDNA encoding *Arabidopsis thaliana* DRT111, a gene that encodes a protein thought to be involved in DNA damage repair. DRT111 nucleic acids and polypeptides, as well as molecules which increase or decrease expression or activity of DRT111, are expected to be useful in the diagnosis and treatment of disorders associated with aberrant DNA damage repair (e.g., drug-resistant cancer).

The DRT111 molecules of the present invention are useful as modulating agents in regulating a variety of cellular processes. Accordingly, in one aspect, this invention provides isolated nucleic acid molecules encoding DRT111 proteins or biologically active portions thereof, as well as nucleic acid fragments suitable as primers or hybridization probes for the detection of DRT111-encoding nucleic acids.

The invention features a nucleic acid molecule which is at least 45% (or 55%, 65%, 75%, 85%, 95%, or 98%) identical to the nucleotide sequence shown in SEQ ID NO:1, or SEQ ID NO:3, or the nucleotide sequence of the cDNA insert of the plasmid deposited with ATCC as Accession Number (the "cDNA of ATCC 209937"), or a complement thereof.

The invention features a nucleic acid molecule which includes a fragment of at least 30 (50, 75, 100, 125, 150, 175, 200, 225, 250, 275, 300, 325, 350, 375, 400, 425, 450, 500, 550, 600, 650, 700, 800, 900, 1000, 1250, 1500, or 1695) nucleotides of the nucleotide sequence shown in SEQ ID NO:1, or SEQ ID NO:3, or the nucleotide sequence of the cDNA ATCC 209937, or a complement thereof.

The invention also features a nucleic acid molecule which includes a nucleotide sequence encoding a protein having an amino acid sequence that is at least 45% (or 55%, 65%, 75%, 85%, 95%, or 98%) identical to the amino acid sequence of SEQ ID NO:2, or the amino acid sequence encoded by the cDNA of ATCC 209937. In a preferred embodiment, a DRT111 nucleic acid molecule has the nucleotide sequence shown SEQ ID NO:1, or SEQ ID NO:3, or the nucleotide sequence of the cDNA of ATCC 209937.

Also within the invention is a nucleic acid molecule which encodes a fragment of a polypeptide having the amino acid sequence of SEQ ID NO:2, the fragment including at least 15 (25, 30, 50, 100, 150, 300, or 400) contiguous amino acids of SEQ ID NO:2 or the polypeptide encoded by the cDNA of ATCC 209937.

The invention includes a nucleic acid molecule which encodes a naturally occurring allelic variant of a polypeptide having the amino acid sequence of SEQ ID NO:2 or an amino acid sequence encoded by the cDNA of ATCC 209937, wherein the nucleic acid molecule hybridizes to a nucleic acid molecule having the nucleotide sequence of SEQ ID NO:1 or SEQ ID NO:3 under stringent conditions.

Also within the invention are isolated nucleic acid molecules which encode a polypeptide having the amino acid sequence of SEQ ID NO:2; isolated nucleic acid molecules which encode a fragment of a polypeptide having the amino acid sequence of SEQ ID NO:2, wherein the fragment contains at least 15 contiguous amino acids of SEQ ID NO:2; and isolated nucleic acid molecules which encode naturally occurring allelic variants of a polypeptide including the amino acid sequence of SEQ ID NO: 2, wherein the nucleic acid molecule hybridizes to a nucleic acid molecule consisting of the nucleotide sequence of SEQ ID NO:1, SEQ ID NO:3, the complement of SEQ ID NO:1, or the complement of SEQ ID NO:3 under stringent conditions. These isolated nucleic acid molecules can have the nucleotide sequence of SEQ ID NO:1, SEQ ID NO:3, the complement of SEQ ID NO:1, or the complement of SEQ ID NO:3; the nucleotide sequence of SEQ ID NO:1, SEQ ID NO:3, the complement of SEQ ID NO:1 or, the complement of SEQ ID NO:3, wherein the "T"s are replaced with "U"s; or fragments of the foregoing that include at least 30 contiguous nucleotides of SEQ ID NO:1, SEQ ID NO:3, the complement of SEQ ID NO:1, or the complement of SEQ ID NO:3.

Another embodiment of the invention features isolated nucleic acid molecules which specifically detect DRT111 nucleic acid molecules relative to non-DRT111 nucleic acid molecules. For example, in one embodiment, such nucleic acid molecules hybridize under stringent conditions to a nucleic acid molecule having the nucleotide sequence of SEQ ID NO:1, SEQ ID NO:3, or the cDNA of ATCC 209937, or a complement thereof. In another embodiment, these nucleic acid molecules are at least 30 (50, 75, 100, 125, 150, 175, 200, 225, 250, 275, 300, 325, 350, 375, 400, 425, 450, 500, 550, 600, 650, 700, 800, 900, 1000, 1250, 1500, or 1695) nucleotides in length and hybridizes under stringent conditions to a nucleic acid molecule having the nucleotide sequence shown in SEQ ID NO:1, SEQ ID NO:3, the cDNA of ATCC 209937, or a complement thereof. In one embodiment, the invention provides an isolated nucleic acid molecule which is antisense to the coding strand of a DRT111 nucleic acid.

Also included in the invention are isolated nucleic acid molecules having a nucleotide sequence which is at least 55% identical to the nucleotide sequence of SEQ ID NO:1 or SEQ ID NO:3, or a complement thereof; those having a nucleotide sequence that hybridizes to a nucleic acid molecule consisting of the nucleotide sequence of SEQ ID NO:1 or SEQ ID NO:3 under stringent conditions, or a complement thereof; and those having a nucleotide sequence that hybridizes to a nucleic acid molecule consisting of the nucleotide sequence of the cDNA insert of the plasmid deposited with ATCC as Accession Number 209937 under stringent conditions, or a complement thereof.

The nucleic acids of the invention can also include other nucleic acid sequences. In various embodiments, the nucleic acids of the invention further include vector nucleic acid sequences or nucleic acid sequences encoding a heterologous polypeptide. Thus, the invention also includes a vector, e.g., a recombinant expression vector, which includes a nucleic acid molecule of the invention.

The invention also features host cells containing a nucleic acid molecule of the invention. In some cases, the host cell is a mammalian cell, such as a non-human mammalian cell. The invention also provides a method for producing a polypeptide of the invention (e.g., human DRT111 protein) by culturing, in a suitable medium, a host cell of the invention containing a recombinant expression vector such that a polypeptide of the invention is produced.

Another aspect of this invention features isolated or recombinant DRT111 proteins and polypeptides. Preferred DRT111 proteins and polypeptides possess at least one biological activity possessed by naturally occurring human DRT111, e.g., the ability to bind proteins involved in DNA repair, the ability to facilitate DNA repair, and the ability to impart cellular resistance to agents that induce DNA damage.

Polypeptides or proteins featured in the invention include: isolated polypeptides having an amino acid sequence that is at least about 45%, preferably 55%, 65%, 75%, 85%, 95%, or 98% identical to the amino acid sequence of SEQ ID NO:2.

Also within the invention are: an isolated polypeptide which is encoded by a nucleic acid molecule having a nucleotide sequence that is at least about 45%, preferably 55%, 65%, 75%, 85%, or 95% identical to SEQ ID NO:3 or the cDNA of ATCC 209937; and an isolated polypeptide which is encoded by a nucleic acid molecule having a nucleotide sequence which hybridizes under stringent hybridization conditions to a nucleic acid molecule having the nucleotide sequence of SEQ ID NO:3 or the non-coding strand of the cDNA of ATCC 209937.

Additional polypeptides of the invention include those encoded by isolated nucleic acid molecules which encode a polypeptide having the amino acid sequence of SEQ ID NO:2; isolated nucleic acid molecules which encode a fragment of a polypeptide having the amino acid sequence of SEQ ID NO:2, wherein the fragment contains at least 15 contiguous amino acids of SEQ ID NO:2; and isolated nucleic acid molecules which encode naturally occurring allelic variants of a polypeptide including the amino acid sequence of SEQ ID NO: 2, wherein the nucleic acid molecule hybridizes to a nucleic acid molecule consisting of the nucleotide sequence of SEQ ID NO:1, SEQ ID NO:3, the complement of SEQ ID NO:1, or the complement of SEQ ID NO:3 under stringent conditions.

Other polypeptides of the invention include: a fragment of a polypeptide having the amino acid sequence of SEQ ID NO:2, wherein the fragment includes at least 17 contiguous amino acids of SEQ ID NO:2; a naturally occurring allelic variant of a polypeptide having the amino acid sequence of SEQ ID NO:2 or an amino acid sequence encoded by the cDNA insert of the plasmid deposited with ATCC as Accession Number 209937, wherein the polypeptide is encoded by a nucleic acid molecule which hybridizes to a nucleic acid molecule consisting of the nucleotide sequence of SEQ ID NO:1 or SEQ ID NO:3 under stringent conditions; and a polypeptide which is encoded by a nucleic acid molecule having a nucleotide sequence which is at least 57% identical to a nucleic acid molecule consisting of the nucleotide sequence of SEQ ID NO:1 or SEQ ID NO:3.

Isolated polypeptides of the invention can have the amino acid sequence of SEQ ID NO:2 or an amino acid sequence encoded by the cDNA insert of the plasmid deposited with ATCC as Accession Number 209937.

The polypeptides of the present invention, or biologically active portions thereof, can be operatively linked to heterologous amino acid sequences to form fusion proteins. The invention further features antibodies that specifically bind to the polypeptides of the invention, such as monoclonal or polyclonal antibodies. In addition, the polypeptides or biologically active portions thereof can be incorporated into pharmaceutical compositions, which optionally include pharmaceutically acceptable carriers.

Methods of producing polypeptides are also included within the invention. One such method includes the step of culturing a host cell containing an isolated nucleic acid molecule which encodes: a polypeptide having the amino acid sequence of SEQ ID NO:2; a fragment of a polypeptide having the amino acid sequence of SEQ ID NO:2, wherein the fragment includes at least 17 contiguous amino acids of SEQ ID NO:2; or a naturally occurring allelic variant of a polypeptide having the amino acid sequence of SEQ ID NO: 2, wherein the nucleic acid molecule hybridizes to a nucleic acid molecule consisting of the nucleotide sequence of SEQ ID NO:1, SEQ ID NO:3, the complement of SEQ ID NO:1, or the complement of SEQ ID NO:3 under stringent conditions; under conditions in which the nucleic acid is expressed.

Another such method for producing polypeptides features the step of culturing a host cell having an isolated nucleic acid molecule encoding: a polypeptide having the amino acid sequence of SEQ ID NO:2 or an amino acid sequence encoded by the cDNA insert of the plasmid deposited with ATCC as Accession Number 209937; a fragment of a polypeptide having the amino acid sequence of SEQ ID NO:2 or an amino acid sequence encoded by the cDNA insert of the plasmid deposited with ATCC as Accession Number 209937, wherein the fragment includes at least 17 contiguous amino acids of SEQ ID NO:2 or an amino acid sequence encoded by the cDNA insert of the plasmid deposited with ATCC as Accession Number 209937; or a naturally occurring allelic variant of a polypeptide having the amino acid sequence of SEQ ID NO:2 or an amino acid sequence encoded by the cDNA insert of the plasmid deposited with ATCC as Accession Number 209937, wherein the polypeptide is encoded by a nucleic acid molecule which hybridizes to a nucleic acid molecule consisting of the nucleotide sequence of SEQ ID NO:1, SEQ ID NO:3, a complement of SEQ ID NO:1, or a complement of SEQ ID NO:3 under stringent conditions; under conditions in which the nucleic acid molecule is expressed.

The invention also includes a method for detecting the presence of a polypeptide of the invention in a sample. This method features the steps of contacting the sample with a compound which selectively binds to the polypeptide and then determining whether the compound binds to a polypeptide in the sample. In some cases, the compound which binds to the polypeptide is an antibody.

Also within the invention is a kit including a compound which selectively binds to a polypeptide of the invention and instructions for use.

Additionally featured in the invention are methods for detecting the presence of a nucleic acid molecule of the invention in a sample. This method includes the steps of contacting the sample with a nucleic acid probe or primer which selectively hybridizes to a nucleic acid molecule of the invention; and then determining whether the nucleic acid probe or primer binds to a nucleic acid molecule in the sample. In many cases, the foregoing sample includes mRNA molecules or genomic DNA.

Also within the invention is a kit including a compound which selectively hybridizes to a nucleic acid molecule of the invention and instructions for use.

Other methods of the invention include those for identifying a compound which binds to a polypeptide featured in the invention. These methods include the steps of contacting a polypeptide of the invention with a test compound and then determining whether the polypeptide binds to the test compound. In various embodiments of these methods, the binding of the test compound to the polypeptide is detected using an assay which measures binding of the test compound to the polypeptide or using a competition binding assay.

The invention also includes a method for modulating the activity of a polypeptide of the invention. This method includes the steps of contacting the polypeptide or a cell expressing the polypeptide with a compound which binds to the polypeptide in a sufficient concentration to modulate the activity of the polypeptide.

In another aspect, the invention provides a method for identifying a compound that binds to or modulates the activity of a polypeptide of the invention (e.g., a DRT111 protein). In general, such methods entail measuring a biological activity of the polypeptide in the presence and absence of a test compound and identifying those compounds which alter the activity of the polypeptide. One such method includes the steps of contacting the polypeptide with a test compound and then determining the effect of the test compound on the activity of the polypeptide (i.e., upregulation or downregulation) to thereby identify a compound which modulates the activity of the polypeptide.

The invention also features methods for identifying a compound which modulates the expression of a nucleic acid or polypeptide of the invention by measuring the expression of the nucleic acid or polypeptide in the presence and absence of a compound.

Other aspects of the invention are methods and compositions relating to drug resistance. A "drug-resistant phenotype" refers to a cellular phenotype which is associated with increased survival after exposure to a drug, e.g., a chemotherapeutic drug, compared to a cell that does not have this phenotype. A "drug-resistant cell" refers to a cell that exhibits this phenotype.

Also within the invention is a method of determining whether a cell has a drug-resistant phenotype by measuring the expression of DRT111 in the cell and comparing this expression to that in a control cell. Increased expression of DRT111 in the cell compared to the control cell indicates that the cell has a drug-resistant phenotype. In one embodiment of this method, DRT111 expression is determined by measuring DRT111 protein. In another embodiment, DRT111 expression is measured using an antibody. In still another embodiment, DRT111 expression is measured by quantifying mRNA encoding DRT111 or the copy number of the DRT111 gene.

The invention also includes a method for modulating the drug resistance of a cell by modulating DRT111 expression or activity within the cell. Thus in one embodiment, the drug-resistance of a cell is reduced by contacting the cell with a molecule that reduces the expression of DRT111 within the cell (e.g., an antisense nucleic acid molecule)

Another aspect of the present invention is a method of improving effectiveness of chemotherapy for a mammal having a disorder associated with the presence of drug-resistant neoplastic cells. In this method, a chemotherapeutic drug and a molecule that reduces expression of DRT111 are co-administered to a mammal.

The invention also includes a method of identifying a compound that modulates the drug resistance of a cell by first contacting the cell with a test compound and then measuring and comparing DRT111 expression in the cell exposed to the compound to DRT111 expression in a control cell not exposed to the compound. The compound is identified as modulator of drug resistance when the level of DRT111 expression in the cell exposed to the compound differs from the level of DRT111 expression in cells not exposed to the compound. In one embodiment of this method, the cell has a drug-resistant phenotype. In another embodiment, the cell is a mammalian cell. This method may also include an optional step of measuring the drug resistance of the cell in the presence of the identified modulator of drug resistance. The DRT111 modulating compounds that are identified in the foregoing methods are also included within the invention.

The invention also features a method of treating a mammal suspected of having a disorder associated with the presence of drug-resistant cells. This method includes the steps of determining whether a mammal has a disorder associated with the presence of drug-resistant cells having increased DRT111 expression (e.g., drug-resistant cancer), and administering to the mammal a compound that sufficiently reduces the expression of DRT111 so that the drug resistance of the cells associated with the disorder is modulated.

Another feature of the invention is a method for treating a patient having a neoplastic disorder (e.g., cancer) by administering to the patient a therapeutically effective amount of a compound that decreases the expression of DRT111.

Also within the invention is a method for increasing drug resistance in a cell having an undesirably low level of DRT111 expression by administering a compound that increases the expression of DRT111.

Other features and advantages of the invention will be apparent from the following detailed description and claims.

BRIEF DESCRIPTION OF THE DRAWINGS

FIG. 1 is a depiction of the nucleotide sequence (SEQ ID NO:1) of a cDNA encoding human DRT111 and the predicted amino acid sequence (SEQ ID NO:2) of human DRT111. The cDNA encoding human DRT111 includes an opening reading frame (SEQ ID NO:3) which extends from nucleotide 145 to nucleotide 1348 of SEQ ID NO: 1.

Figure 2A:
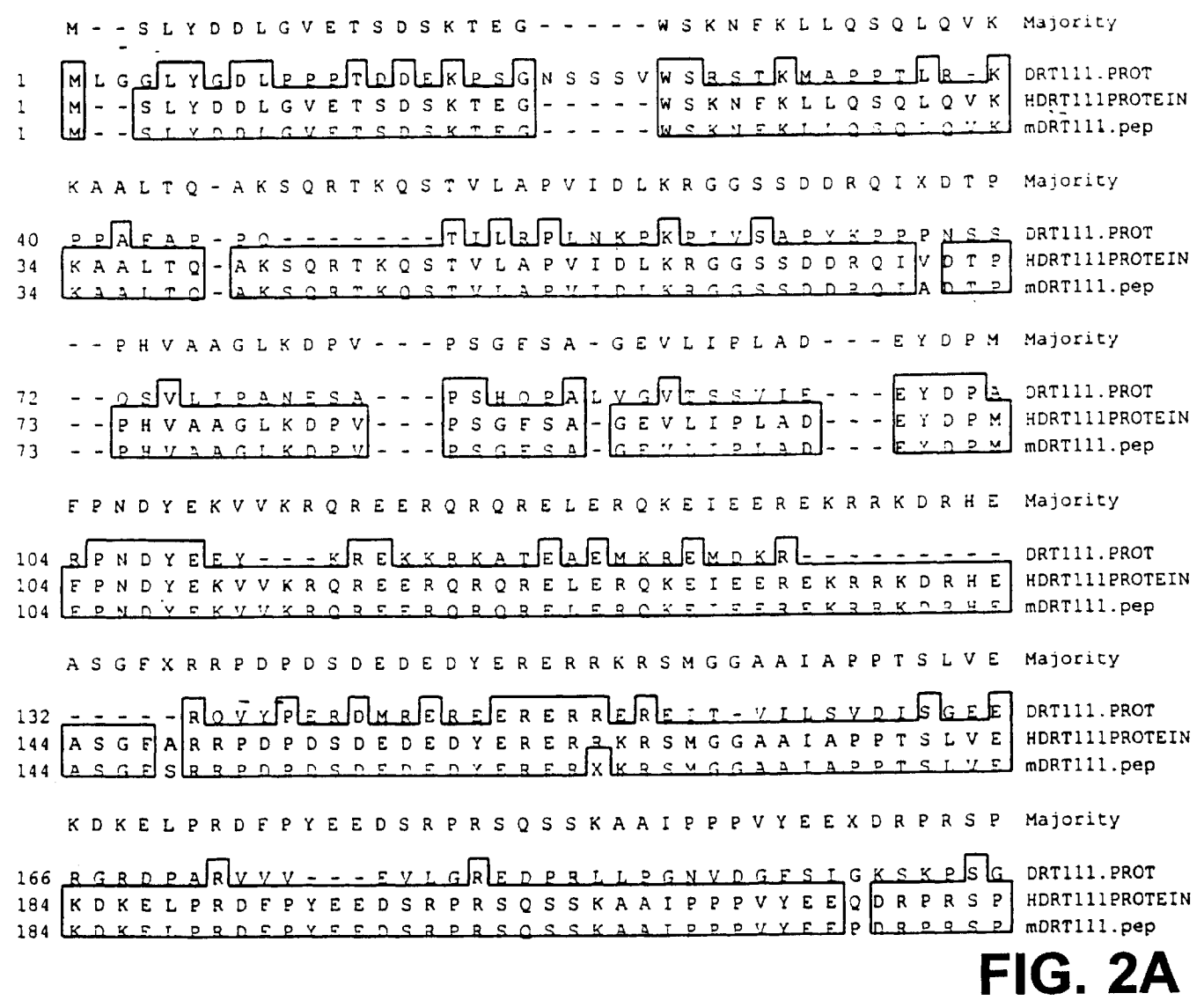

FIGS. 2A–2B is a comparison of the amino acid sequence of murine DRT111 (SEQ ID NO:7; "mDRT111.pep"), human DRT111 (SEQ ID NO: 2; "HDRT111PROTEIN"), and *A. thaliana* DRT111 ("DRT111.PROT").

FIG. 3 is a depiction of the nucleotide sequence of a cDNA encoding murine DRT111 (SEQ ID NO:6) and the amino acid sequence of murine DRT111 (SEQ ID NO:7).

DETAILED DESCRIPTION OF THE INVENTION

Figure 4:
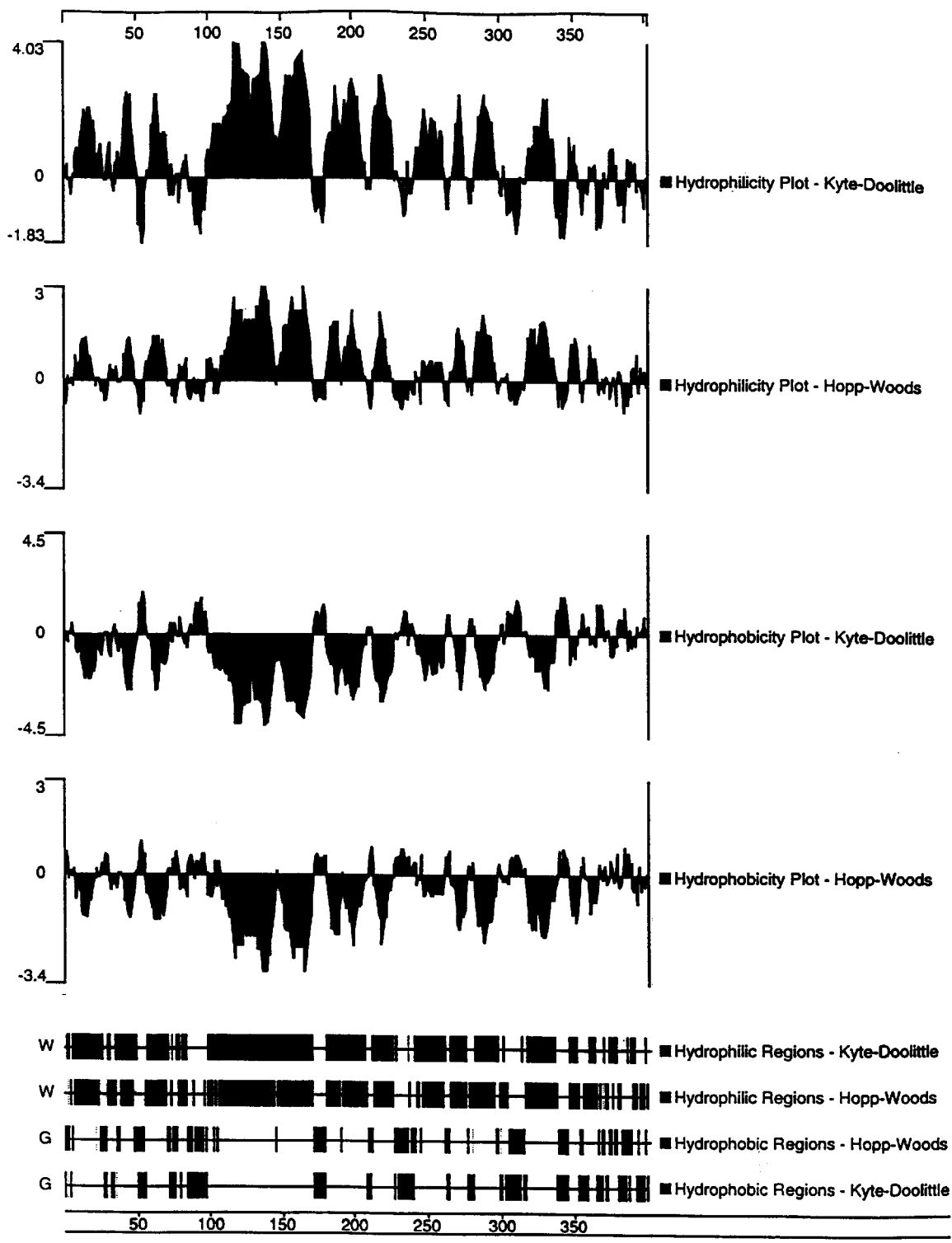
FIG. 4 is a depiction of hydrophilicity and hydrophobicity plots of human DRT111.

The present invention is based on the discovery of a cDNA molecule encoding human DRT111, a protein associated with resistance to cyclophosphamide.

A nucleotide sequence encoding a human DRT111 protein (SEQ ID NO:1) and the predicted amino acid sequence of human DRT111 protein (SEQ ID NO: 2) is shown in FIG. 1. The open reading frame of the nucleotide sequence of human DRT111 (SEQ ID NO:3) is also shown in FIG. 1.

The DRT111 cDNA of SEQ ID NO:1, which is approximately 1695 nucleotides long including untranslated regions, encodes a protein having a molecular weight of approximately 44,960 Da (excluding post-translational modifications). A plasmid containing a cDNA encoding human DRT111 (with the cDNA insert name of fohq002DR) was deposited with American Type Culture Collection (ATCC), 10801 University Boulevard, Manassas, Va. 20110-2209 on Jun. 2, 1998 and assigned Accession Number 209937. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Human DRT111 is one member of a family of molecules (the "DRT111 family") having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

Preferred DRT111 polypeptides of the present invention have an amino acid sequence sufficiently identical to the amino acid sequence of SEQ ID NO:2. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "DRT111 activity", "biological activity of DRT111" or "functional activity of DRT111", refers to an activity exerted by a DRT111 protein, polypeptide or nucleic acid molecule on a DRT111 responsive cell as determined in vivo, or in vitro, according to standard techniques. A DRT111 activity can be a direct activity, such as an association with or an enzymatic activity on a second protein or nucleic acid or an indirect activity, e.g., altered drug resistance mediated by interaction of the DRT111 protein with a second protein or nucleic acid. In a preferred embodiment, a DRT111 activity includes at least one or more of the following activities: the ability to bind proteins involved in DNA repair, the ability to facilitate DNA repair, the ability to bind a nucleic acid molecule, and the ability to impart cellular resistance to chemotherapeutic drugs. Accordingly, another embodiment of the invention features isolated DRT111 proteins and polypeptides having a DRT111 activity.

Various aspects of the invention are described in further detail in the following subsections.

I. Isolated Nucleic Acid Molecules

One aspect of the invention pertains to isolated nucleic acid molecules that encode DRT111 proteins or biologically active portions thereof, as well as nucleic acid molecules sufficient for use as hybridization probes to identify DRT111-encoding nucleic acids (e.g., DRT111 mRNA) and fragments for use as PCR primers for the amplification or mutation of DRT111 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated DRT111 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, or the cDNA of ATCC 209937, or a complement of any of these nucleotide sequences, can be isolated using standard molecular biology techniques and the sequence information provided herein. Using all or portion of the nucleic acid sequences of SEQ ID NO:1, SEQ ID NO:3, or the cDNA of ATCC 209937 as a hybridization probe, DRT111 nucleic acid molecules can be isolated using standard hybridization and cloning techniques (e.g., as described in Sambrook et al., eds., *Molecular Cloning: A Laboratory Manual.* 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to DRT111 nucleotide sequences can be prepared by standard synthetic techniques, e.g., using an automated DNA synthesizer.

In another preferred embodiment, an isolated nucleic acid molecule of the invention includes a nucleic acid molecule which is a complement of the nucleotide sequence shown in SEQ ID NO:1, SEQ ID NO:3, or the cDNA of ATCC 209937, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding DRT111, for example, a fragment which can be used as a probe or primer or a fragment encoding a biologically active portion of DRT111. The nucleotide sequence determined from the cloning of the human DRT111 gene allows for the generation of probes and primers designed for use in identifying and/or cloning DRT111 homologues in other cell types, e.g., from other tissues, as well as DRT111 homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, or the cDNA of ATCC 209937 or of a naturally occurring mutant of SEQ ID NO:1, SEQ ID NO:3, or the cDNA of ATCC 209937.

Probes based on the human DRT111 nucleotide sequence can be used to detect transcripts or genomic sequences encoding the same or identical proteins. The probe comprises a label group attached thereto, e.g., a radioisotope, a fluorescent compound, an enzyme, or an enzyme co-factor. Such probes can be used as a part of a diagnostic test kit for identifying cells or tissue which mis-express a DRT111 protein, such as by measuring a level of a DRT111-encoding nucleic acid in a sample of cells from a subject, e.g., detecting DRT111 mRNA levels or determining whether a genomic DRT111 gene has been mutated, deleted, or amplified.

A nucleic acid fragment encoding a "biologically active portion of DRT111" can be prepared by isolating a portion of SEQ ID NO:1, SEQ ID NO:3, or the nucleotide sequence of the cDNA of ATCC 209937 which encodes a polypeptide having a DRT111 biological activity, expressing the encoded portion of DRT111 protein (e.g., by recombinant expression in vitro) and assessing the activity of the encoded portion of DRT111. Examples of such nucleic acid fragments include those that encode a biologically active portion of DRT111, e.g. polynucleotides encoding polypeptides having homology to the amino acid sequence of *A. thaliana* DRT111 protein.

The invention further encompasses nucleic acid molecules that differ from the nucleotide sequence of SEQ ID NO:1, SEQ ID NO:3, or the cDNA of ATCC 209937 due to degeneracy of the genetic code and thus encode the same DRT111 protein as that encoded by the nucleotide sequence shown in SEQ ID NO:1, SEQ ID NO:3, or the cDNA of ATCC 209937.

In addition to the human DRT111 nucleotide sequence shown in SEQ ID NO:1, SEQ ID NO:3, or the cDNA of ATCC 209937, it will be appreciated by those skilled in the art that DNA sequence polymorphisms that lead to changes in the amino acid sequences of DRT111 may exist within a population (e.g., the human population). Such genetic polymorphism in the DRT111 gene may exist among individuals within a population due to natural allelic variation. As used herein, the terms "gene" and "recombinant gene" refer to nucleic acid molecules comprising an open reading frame encoding a DRT111 protein, preferably a mammalian DRT111 protein. Such natural allelic variations can typically result in 1–5% variance in the nucleotide sequence of the DRT111 gene. Any and all such nucleotide variations and resulting amino acid polymorphisms in DRT111 that are the result of natural allelic variation and that do not alter the functional activity of DRT111 are intended to be within the scope of the invention.

Moreover, nucleic acid molecules encoding DRT111 proteins from other species (DRT111 homologues), which have a nucleotide sequence which differs from that of a human DRT111, are intended to be within the scope of the invention. Nucleic acid molecules corresponding to natural allelic variants and homologues of the DRT111 cDNA of the invention can be isolated based on their identity to the human DRT111 nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 300 (325, 350, 375, 400, 425, 450, 500, 550, 600, 650, 700, 800, 900, 1000, 1250, 1500, or 1695) nucleotides in length and hybridizes under stringent conditions to the nucleic acid molecule comprising the nucleotide sequence, preferably the coding sequence, of SEQ ID NO:1, SEQ ID NO:3, or the cDNA of ATCC 209937.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, the cDNA of ATCC 209937 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the DRT111 sequence that may exist in the population, the skilled artisan will further appreciate that changes can be introduced by mutation into the nucleotide sequence of SEQ ID NO:1, SEQ ID NO:3, the cDNA of ATCC 209937, thereby leading to changes in the amino acid sequence of the encoded DRT111 protein, without altering the functional ability of the DRT111 protein. For example, one can make nucleotide substitutions leading to amino acid substitutions at "non-essential" amino acid residues. A "non-essential" amino acid residue is a residue that can be altered from the wild-type sequence of DRT111 (e.g., the sequence of SEQ ID NO:2) without altering the biological activity, whereas an "essential" amino acid residue is required for biological activity. For example, amino acid residues that are conserved among the DRT111 proteins of various species are predicted to be particularly unamenable to alteration.

For example, preferred DRT111 proteins of the present invention retain homology to DRT111 protein of A. thaliana. Such conserved amino acid regions are less likely to be amenable to mutation. Other amino acid residues, however, (e.g., those that are not conserved or only semi-conserved among DRT111 of various species) may not be essential for activity and thus are likely to be amenable to alteration.

Accordingly, another aspect of the invention pertains to nucleic acid molecules encoding DRT111 proteins that contain changes in amino acid residues that are not essential for activity. Such DRT111 proteins differ in amino acid sequence from SEQ ID NO:2 yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2.

An isolated nucleic acid molecule encoding a DRT111 protein having a sequence which differs from that of SEQ ID NO:2 can be created by introducing one or more nucleotide substitutions, additions or deletions into the nucleotide sequence of SEQ ID NO:1, SEQ ID NO:3, the cDNA of ATCC 209937 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues: A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in DRT111 is preferably replaced with another amino acid residue from the same side chain family. Alternatively, mutations can be introduced randomly along all or part of a DRT111 coding sequence, such as by saturation mutagenesis, and the resultant mutants can be screened for DRT111 biological activity to identify mutants that retain activity. Following mutagenesis, the encoded protein can be expressed recombinantly and the activity of the protein can be determined.

In a preferred embodiment, a mutant DRT111 protein can be assayed for: the ability to bind proteins involved in DNA repair, the ability to facilitate DNA repair, or the ability to impart cellular resistance to agents that induce DNA damage.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire DRT111 coding strand, or to only a portion thereof, e.g., all or part of the protein coding region (or open reading frame). An antisense nucleic acid molecule can be antisense to a noncoding region of the coding strand of a nucleotide sequence encoding DRT111. The noncoding regions ("5' and 3' untranslated regions") are the 5' and 3' sequences which flank the coding region and are not translated into amino acids.

Given the coding strand sequences encoding DRT111 disclosed herein (e.g., SEQ ID NO:1 or SEQ ID NO:3), antisense nucleic acids of the invention can be designed according to the rules of Watson and Crick base pairing. The antisense nucleic acid molecule can be complementary to the entire coding region of DRT111 mRNA, but more preferably is an oligonucleotide which is antisense to only a portion of the coding or noncoding region of DRT111 mRNA. For example, the antisense oligonucleotide can be complementary to the region surrounding the translation start site of DRT111 mRNA, e.g., AAACTGAAGAAAA-GATGTCCCTGTACGATG (SEQ ID NO:4) or GAAAA-GATGTCCCTGTACGATGACC (SEQ ID NO:5). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)

w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a DRT111 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave DRT111 mRNA transcripts to thereby inhibit translation of DRT111 mRNA. A ribozyme having specificity for a DRT111-encoding nucleic acid can be designed based upon the nucleotide sequence of a DRT111 cDNA disclosed herein (e.g., SEQ ID NO:1, SEQ ID NO:3). For example, a derivative of a Tetrahymena L-19 IVS RNA can be constructed in which the nucleotide sequence of the active site is complementary to the nucleotide sequence to be cleaved in a DRT111-encoding mRNA. See, e.g., Cech et al. U.S. Pat. No. 4,987,071; and Cech et al. U.S. Pat. No. 5,116,742. Alternatively, DRT111 mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, DRT111 gene expression can be inhibited by targeting nucleotide sequences complementary to the regulatory region of the DRT111 (e.g., the DRT111 promoter and/or enhancers) to form triple helical structures that prevent transcription of the DRT111 gene in target cells. See generally, Helene (1991) *Anticancer Drug Des.* 6(6):569–84; Helene (1992) *Ann. N.Y. Acad. Sci.* 660:27–36; and Maher (1992) *Bioassays* 14(12):807–15.

In preferred embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci. USA* 93: 14670–675.

PNAs of DRT111 can be used for therapeutic and diagnostic applications. For example, PNAs can be used as antisense or antigene agents for sequence-specific modulation of gene expression by, e.g., inducing transcription or translation arrest or inhibiting replication. PNAs of DRT111 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence analysis and hybridization (Hyrup (1996) supra; Perry-O'Keefe et al. (1996) *Proc. Natl. Acad. Sci. USA* 93: 14670–675).

In another embodiment, PNAs of DRT111 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of DRT111 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) *Nucleic Acids Research* 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a linker between the PNA and the 5' end of DNA (Mag et al. (1989) *Nucleic Acid Res.* 17:5973–88). PNA monomers are then coupled in a stepwise manner to produce a chimeric molecule with a 5' PNA segment and a 3' DNA segment (Finn et al. (1996) *Nucleic Acids Research* 24(17) :3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio/Techniques* 6:958–976) or intercalating agents (See, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated DRT111 Proteins and Anti-DRT111 Antibodies

One aspect of the invention pertains to isolated DRT111 proteins, and biologically active portions thereof, as well as polypeptide fragments suitable for use as immunogens to raise anti-DRT111 antibodies. In one embodiment, native DRT111 proteins can be isolated from cells or tissue sources by an appropriate purification scheme using standard protein purification techniques. In another embodiment, DRT111 proteins are produced by recombinant DNA techniques. Alternative to recombinant expression, a DRT111 protein or polypeptide can be synthesized chemically using standard peptide synthesis techniques.

An "isolated" or "purified" protein or biologically active portion thereof is substantially free of cellular material or other contaminating proteins from the cell or tissue source from which the DRT111 protein is derived, or substantially free from chemical precursors or other chemicals when chemically synthesized. The language "substantially free of cellular material" includes preparations of DRT111 protein in which the protein is separated from cellular components of the cells from which it is isolated or recombinantly produced. Thus, DRT111 protein that is substantially free of cellular material includes preparations of DRT111 protein having less than about 30%, 20%, 10%, or 5% (by dry weight) of non-DRT111 protein (also referred to herein as a "contaminating protein"). When the DRT111 protein or biologically active portion thereof is recombinantly produced, it is also preferably substantially free of culture medium, i.e., culture medium represents less than about 20%, 10%, or 5% of the volume of the protein preparation. When DRT111 protein is produced by chemical synthesis, it is preferably substantially free of chemical precursors or other chemicals, i.e., it is separated from chemical precursors or other chemicals which are involved in the synthesis of the protein. Accordingly such preparations of DRT111 protein have less than about 30%, 20%, 10%, 5% (by dry weight) of chemical precursors or non-DRT111 chemicals.

Biologically active portions of a DRT111 protein include peptides comprising amino acid sequences sufficiently identical to or derived from the amino acid sequence of the DRT111 protein (e.g., the amino acid sequence shown in SEQ ID NO:2), which include less amino acids than the full length DRT111 proteins, and exhibit at least one activity of a DRT111 protein. Typically, biologically active portions comprise a domain or motif with at least one activity of the DRT111 protein. A biologically active portion of a DRT111 protein can be a polypeptide which is, for example, 10, 25, 50, 100 or more amino acids in length. Preferred biologically active polypeptides include those that share homology to portions of the amino acid sequence of *A. thaliana* DRT111 protein or murine DRT111 protein (SEQ ID NO:7).

Moreover, other biologically active portions, in which other regions of the protein are deleted, can be prepared by recombinant techniques and evaluated for one or more of the functional activities of a native DRT111 protein. A preferred DRT111 protein has the amino acid sequence shown of SEQ ID NO:2. Other useful DRT111 proteins are substantially identical to SEQ ID NO:2 and retain the functional activity of the protein of SEQ ID NO:2 yet differ in amino acid sequence due to natural allelic variation or mutagenesis. Accordingly, a useful DRT111 protein is a protein which includes an amino acid sequence at least about 45%, preferably 55%, 65%, 75%, 85%, 95%, or 99% identical to the amino acid sequence of SEQ ID NO:2 and retains the functional activity of the DRT111 proteins of SEQ ID NO:2. In a preferred embodiment, the DRT111 protein retains the functional activity of the DRT111 protein of SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Nat'l Acad. Sci. USA* 87:2264–2268, modified as in Karlin and Altschul (1993) *Proc. Nat'l Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to DRT111 nucleic acid molecules of the invention. BLAST protein searches can be performed with the XBLAST program, score=50, wordlength=3 to obtain amino acid sequences homologous to DRT111 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides DRT111 chimeric or fusion proteins. As used herein, a DRT111 "chimeric protein" or "fusion protein" comprises a DRT111 polypeptide operatively linked to a non-DRT111 polypeptide. A "DRT111 polypeptide" refers to a polypeptide having an amino acid sequence corresponding to DRT111, whereas a "non-DRT111 polypeptide" refers to a polypeptide having an amino acid sequence corresponding to a protein which is not substantially identical to the DRT111 protein, e.g., a protein which is different from the DRT111 protein and which is derived from the same or a different organism. Within a DRT111 fusion protein the DRT111 polypeptide can correspond to all or a portion of a DRT111 protein, preferably at least one biologically active portion of a DRT111 protein. Within the fusion protein, the term "operatively linked" is intended to indicate that the DRT111 polypeptide and the non-DRT111 polypeptide are fused in-frame to each other. The non-DRT111 polypeptide can be fused to the N-terminus or C-terminus of the DRT111 polypeptide.

One useful fusion protein is a GST-DRT111 fusion protein in which the DRT111 sequences are fused to the C-terminus of the GST sequences. Such fusion proteins can facilitate the purification of recombinant DRT111.

In yet another embodiment, the fusion protein is an DRT111-immunoglobulin fusion protein in which all or part of DRT111 is fused to sequences derived from a member of the immunoglobulin protein family. DRT111-immunoglobulin fusion proteins of the invention can be used as immunogens to produce anti-DRT111 antibodies in a subject, to purify DRT111 ligands and in screening assays to identify molecules which inhibit the interaction of DRT111 with a protein or nucleic acid which binds DRT111.

Preferably, a DRT111 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al. eds., John Wiley & Sons: 1992). Moreover, many expression vectors are commercially available that already encode a fusion moiety (e.g., a GST polypeptide). An DRT111-encoding nucleic acid can be cloned into such an expression vector such that the fusion moiety is linked in-frame to the DRT111 protein.

The present invention also pertains to variants of the DRT111 proteins which function as either DRT111 agonists (mimetics) or as DRT111 antagonists. Variants of the DRT111 protein can be generated by mutagenesis, e.g., discrete point mutation or truncation of the DRT111 protein. An agonist of the DRT111 protein can retain substantially the same, or a subset, of the biological activities of the naturally occurring form of the DRT111 protein. An antagonist of the DRT111 protein can inhibit one or more of the activities of the naturally occurring form of the DRT111 protein by, for example, competitively binding to polynucleotides or proteins involved in DRT111 function. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the DRT111 proteins.

Variants of the DRT111 protein which function as either DRT111 agonists (mimetics) or as DRT111 antagonists can be identified by screening combinatorial libraries of mutants, e.g., truncation mutants, of the DRT111 protein for DRT111 protein agonist or antagonist activity. In one embodiment, a variegated library of DRT111 variants is generated by combinatorial mutagenesis at the nucleic acid level and is encoded by a variegated gene library. A variegated library of DRT111 variants can be produced by, for example, enzymatically ligating a mixture of synthetic oligonucleotides into gene sequences such that a degenerate set of potential DRT111 sequences is expressible as individual polypeptides, or alternatively, as a set of larger fusion proteins (e.g., for phage display) containing the set of DRT111 sequences therein. There are a variety of methods which can be used to produce libraries of potential DRT111 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential DRT111 sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the DRT111 protein coding sequence can be used to generate a variegated population of DRT111 fragments for screening and subsequent selection of variants of a DRT111 protein. In one embodiment, a library of coding sequence fragments can be generated by treating a double stranded PCR fragment of a DRT111 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the DRT111 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of DRT111 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify DRT111 variants (Arkin and Yourvan (1992) *Proc. Natl. Acad. Sci. USA* 89:7811–7815; Delgrave et al. (1993) *Protein Engineering* 6(3):327–331).

An isolated DRT111 protein, or a portion or fragment thereof, can be used as an immunogen to generate antibodies that bind DRT111 using standard techniques for polyclonal and monoclonal antibody preparation. The full-length DRT111 protein can be used or, alternatively, the invention provides antigenic peptide fragments of DRT111 for use as immunogens. The antigenic peptide of DRT111 comprises at least 8 (preferably 10, 15, 20, or 30) amino acid residues of the amino acid sequence shown in SEQ ID NO:2 and encompasses an epitope of DRT111 such that an antibody raised against the peptide forms a specific immune complex with DRT111.

Preferred epitopes encompassed by the antigenic peptide are regions of DRT111 that are located on the surface of the protein, e.g., hydrophilic regions. A hydrophobicity analysis of the human DRT111 protein sequence indicates that the regions between, e.g., amino acids 100 and 170, between amino acids 180 and 207, and between amino acids 240 and 260 of SEQ ID NO:2 are particularly hydrophilic and, therefore, are likely to encode surface residues useful for targeting antibody production.

A DRT111 immunogen typically is used to prepare antibodies by immunizing a suitable subject, (e.g., rabbit, goat, mouse or other mammal) with the immunogen. An appropriate immunogenic preparation can contain, for example, recombinantly expressed DRT111 protein or a chemically synthesized DRT111 polypeptide. The preparation can further include an adjuvant, such as Freund's complete or incomplete adjuvant, or similar immunostimulatory agent. Immunization of a suitable subject with an immunogenic DRT111 preparation induces a polyclonal anti-DRT111 antibody response.

Accordingly, another aspect of the invention pertains to anti-DRT111 antibodies. The term "antibody" as used herein refers to immunoglobulin molecules and immunologically active portions of immunoglobulin molecules, i.e., molecules that contain an antigen binding site which specifically binds an antigen, such as DRT111. A molecule which specifically binds to DRT111 is a molecule which binds DRT111, but does not substantially bind other molecules in a sample, e.g., a biological sample, which naturally contains DRT111. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind DRT111. The term "monoclonal antibody" or "monoclonal antibody composition", as used herein, refers to a population of antibody molecules that contain only one species of an antigen binding site capable of immunoreacting with a particular epitope of DRT111. A monoclonal antibody composition thus typically displays a single binding affinity for a particular DRT111 protein with which it immunoreacts.

Polyclonal anti-DRT111 antibodies can be prepared as described above by immunizing a suitable subject with a DRT111 immunogen. The anti-DRT111 antibody titer in the immunized subject can be monitored over time by standard techniques, such as with an enzyme linked immunosorbent assay (ELISA) using immobilized DRT111. If desired, the antibody molecules directed against DRT111 can be isolated from the mammal (e.g., from the blood) and further purified by well-known techniques, such as protein A chromatography to obtain the IgG fraction. At an appropriate time after immunization, e.g., when the anti-DRT111 antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a DRT111 immunogen as described above, and the culture supernatants of the resulting hybridoma cells are screened to identify a hybridoma producing a monoclonal antibody that binds DRT111.

Any of the many well known protocols used for fusing lymphocytes and immortalized cell lines can be applied for the purpose of generating an anti-DRT111 monoclonal antibody (see, e.g., Current Protocols in Immunology, supra; Galfre et al. (1977) *Nature* 266:55052; R. H. Kenneth, in *Monoclonal Antibodies: A New Dimension In Biological Analyses*, Plenum Publishing Corp., New York, N.Y. (1980); and Lerner (1981) *Yale J. Biol. Med.*, 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind DRT111, e.g., using a standard ELISA assay.

Alternative to preparing monoclonal antibody-secreting hybridomas, a monoclonal anti-DRT111 antibody can be identified and isolated by screening a recombinant combinatorial immunoglobulin library (e.g., an antibody phage display library) with DRT111 to thereby isolate immunoglobulin library members that bind DRT111. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734.

Additionally, recombinant anti-DRT111 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-DRT111 antibody (e.g., monoclonal antibody) can be used to isolate DRT111 by standard techniques, such as affinity chromatography or immunoprecipitation. An anti-DRT111 antibody can facilitate the purification of natural DRT111 from cells and of recombinantly produced DRT111 expressed in host cells. Moreover, an anti-DRT111 antibody can be used to detect DRT111 protein (e.g., in a cellular lysate or cell supernatant) in order to evaluate the abundance and pattern of expression of the DRT111 protein. Anti-DRT111 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding DRT111 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often. in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., DRT111 proteins, mutant forms of DRT111, fusion proteins, etc.).

The recombinant expression vectors of the invention can be designed for expression of DRT111 in prokaryotic or eukaryotic cells, e.g., bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc;

Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the DRT111 expression vector is a yeast expression vector. Examples of vectors for expression in yeast *S. cerivisae* include pYepSec1 (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and picz (InVitrogen Corp, San Diego, Calif.).

Alternatively, DRT111 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to DRT111 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes See Weintraub et al., *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, DRT111 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest.

Preferred selectable markers include those which confer resistance to drugs, such as G418, hygromycin and methotrexate. Nucleic acid encoding a selectable marker can be introduced into a host cell on the same vector as that encoding DRT111 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) DRT111 protein. Accordingly, the invention further provides methods for producing DRT111 protein using the host cells of the invention. In one embodiment, the method comprises culturing the host cell of invention (into which a recombinant expression vector encoding DRT111 has been introduced) in a suitable medium such that DRT111 protein is produced. In another embodiment, the method further comprises isolating DRT111 from the medium or the host cell.

The host cells of the invention can also be used to produce nonhuman transgenic animals. For example, in one embodiment, a host cell of the invention is a fertilized oocyte or an embryonic stem cell into which DRT111-coding sequences have been introduced. Such host cells can then be used to create non-human transgenic animals in which exogenous DRT111 sequences have been introduced into their genome or homologous recombinant animals in which endogenous DRT111 sequences have been altered. Such animals are useful for studying the function and/or activity of DRT111 and for identifying and/or evaluating modulators of DRT111 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous DRT111 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing DRT111-encoding nucleic acid into the male pronuclei of a fertilized oocyte, e.g., by microinjection, retroviral infection, and allowing the oocyte to develop in a pseudopregnant female foster animal. The DRT111 cDNA sequence e.g., that of (SEQ ID NO:1, SEQ ID NO:3, or the cDNA of ATCC 209937) can be introduced as a transgene into the genome of a non-human animal. Alternatively, a nonhuman homologue of the human DRT111 gene, such as a mouse DRT111 gene, can be isolated based on hybridization to the human DRT111 cDNA and used as a transgene. Intronic sequences and polyadenylation signals can also be included in the transgene to increase the efficiency of expression of the transgene. A tissue-specific regulatory sequence(s) can be operably linked to the DRT111 transgene to direct expression of DRT111 protein to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the DRT111 transgene in its genome and/or expression of DRT111 mRNA in tissues or cells of the animals. A transgenic founder animal can then be used to breed additional animals carrying the transgene. Moreover, transgenic animals carrying a transgene encoding DRT111 can further be bred to other transgenic animals carrying other transgenes.

To create an homologous recombinant animal, a vector is prepared which contains at least a portion of a DRT111 gene (e.g., a human or a non-human homolog of the DRT111 gene, e.g., a murine DRT111 gene) into which a deletion, addition or substitution has been introduced to thereby alter, e.g., functionally disrupt, the DRT111 gene. In a preferred embodiment, the vector is designed such that, upon homologous recombination, the endogenous DRT111 gene is functionally disrupted (i.e., no longer encodes a functional protein; also referred to as a "knock out" vector). Alternatively, the vector can be designed such that, upon homologous recombination, the endogenous DRT111 gene is mutated or otherwise altered but still encodes functional protein (e.g., the upstream regulatory region can be altered to thereby alter the expression of the endogenous DRT111 protein). In the homologous recombination vector, the altered portion of the DRT111 gene is flanked at its 5' and 3' ends by additional nucleic acid of the DRT111 gene to allow for homologous recombination to occur between the exogenous DRT111 gene carried by the vector and an endogenous DRT111 gene in an embryonic stem cell. The additional flanking DRT111 nucleic acid is of sufficient length for successful homologous recombination with the endogenous gene. Typically, several kilobases of flanking DNA (both at the 5' and 3' ends) are included in the vector (see e.g., Thomas and Capecchi (1987) *Cell* 51:503 for a description of homologous recombination vectors). The vector is introduced into an embryonic stem cell line (e.g., by electroporation) and cells in which the introduced DRT111 gene has homologously recombined with the endogenous DRT111 gene are selected (see e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach,* Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The DRT111 nucleic acid molecules, DRT111 proteins, and anti-DRT111 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A DRT111 protein likely interacts with other cellular components and can thus be used for (i) modulation of DNA repair; (ii) modulation of cellular resistance to chemotherapeutic drugs; and (iii) regulation of genomic mutation. The isolated nucleic acid molecules of the invention can be used to express DRT111 protein (e.g., via a recombinant expression vector in a host cell in gene therapy applications), to detect DRT111 mRNA or DRT111 genomic DNA (e.g., in a biological sample) or a lesion in a DRT111 gene (e.g., point mutation, base additions or deletions, or gene deletions or amplications), and to modulate DRT111 activity. In addition, the DRT111 proteins can be used to screen drugs or compounds which modulate the DRT111 activity or expression as well as to treat disorders characterized by insufficient or excessive production of DRT111 protein or production of DRT111 protein forms which have decreased or aberrant activity compared to DRT111 wild type protein. In addition, the anti-DRT111 antibodies of the invention can be used to detect and isolate DRT111 proteins and modulate DRT111 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to DRT111 proteins or have a stimulatory or inhibitory effect on, for example, DRT111 expression or DRT111 activity.

In one embodiment, the invention provides assays for screening candidate or test compounds which bind to or modulate the activity of a DRT111 protein or polypeptide or biologically active portion thereof. The test compounds of the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam, (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; and Felici (1991) *J. Mol. Biol.* 222:301–310).

In one embodiment, an assay is a cell-based assay in which a cell which expresses a DRT111 protein, or a biologically active portion thereof, is contacted with a test compound and the ability of the test compound to bind to a DRT111 protein determined. The cell, for example, can be a yeast cell or a cell of mammalian origin. Determining the ability of the test compound to bind to the DRT111 protein can be accomplished, for example, by coupling the test compound with a radioisotope or enzymatic label such that binding of the test compound to the DRT111 protein or biologically active portion thereof can be determined by detecting the labeled compound in a complex. For example, test compounds can be labeled with $^{125}$I, $^{35}$S, $^{14}$C, or $^3$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a DRT111 protein, or a biologically active portion thereof, with a known compound which binds DRT111 to form an assay mixture, contacting the assay mixture with a test compound, and determining the ability of the test compound to interact with a DRT111 protein, wherein determining the ability of the test compound to interact with a DRT111 protein comprises determining the ability of the test compound to preferentially bind to DRT111 or a biologically active portion thereof as compared to the known compound.

In another embodiment, an assay is a cell-based assay comprising contacting a cell expressing a DRT111 protein, or a biologically active portion thereof, with a test compound and determining the ability of the test compound to modulate (e.g., stimulate or inhibit) the activity of the DRT111 protein or biologically active portion thereof. Determining the ability of the test compound to modulate the activity of DRT111 or a biologically active portion thereof can be accomplished, for example, by determining the ability of the DRT111 protein to bind to or interact with a DRT111 target molecule. As used herein, a "target molecule" is a molecule with which a DRT111 protein binds or interacts in nature, for example, a molecule in the nucleus or cytoplasm of a cell which expresses a DRT111 protein. A DRT111 target molecule can be a non-DRT111 molecule or a DRT111 protein or polypeptide of the present invention. In one embodiment, a DRT111 target molecule is part of a multicomponent DNA repair complex that facilitates repair of damaged DNA by binding and excising a section of damaged DNA and replacing it with undamaged DNA. The target, for example, can be a second intracellular protein which has catalytic activity or a protein which facilitates the association of DNA with DRT111.

Determining the ability of the DRT111 protein to bind to or interact with a DRT111 target molecule can be accomplished by one of the methods described above for determining direct binding. In a preferred embodiment, determining the ability of the DRT111 protein to bind to or interact with a DRT111 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target an appropriate substrate, detecting the induction of a reporter gene (e.g., a DRT111-responsive regulatory element operatively linked to a nucleic acid encoding a detectable marker, e.g. luciferase), or detecting a cellular response, for example, cell survival, cellular differentiation, or cell proliferation.

In yet another embodiment, an assay of the present invention is a cell-free assay comprising contacting a DRT111 protein or biologically active portion thereof with a test compound and determining the ability of the test compound to bind to the DRT111 protein or biologically active portion thereof. Binding of the test compound to the DRT111 protein can be determined either directly or indirectly as described above. In a preferred embodiment, the assay includes contacting the DRT111 protein or biologically active portion thereof with a known compound which binds DRT111 to form an assay mixture, contacting the assay mixture with a test compound, and determining the ability of the test compound to interact with a DRT111 protein, wherein determining the ability of the test compound to interact with a DRT111 protein comprises determining the ability of the test compound to preferentially bind to DRT111 or biologically active portion thereof as compared to the known compound.

In another embodiment, an assay is a cell-free assay comprising contacting DRT111 protein or biologically active portion thereof with a test compound and determining the ability of the test compound to modulate (e.g., stimulate or inhibit) the activity of the DRT111 protein or biologically active portion thereof. Determining the ability of the test compound to modulate the activity of DRT111 can be accomplished, for example, by determining the ability of the DRT111 protein to bind to a DRT111 target molecule by one of the methods described above for determining direct binding. In an alternative embodiment, determining the ability of the test compound to modulate the activity of DRT111 can be accomplished by determining the ability of the DRT111 protein further modulate a DRT111 target molecule. For example, the catalytic/enzymatic activity of the target molecule on an appropriate substrate can be determined as previously described.

In yet another embodiment, the cell-free assay comprises contacting the DRT111 protein or biologically active portion thereof with a known compound which binds DRT111 to form an assay mixture, contacting the assay mixture with a test compound, and determining the ability of the test compound to interact with a DRT111 protein, wherein determining the ability of the test compound to interact with a DRT111 protein comprises determining the ability of the DRT111 protein to preferentially bind to or modulate the activity of a DRT111 target molecule.

The cell-free assays of the present invention are amenable to use of both native and variant forms (e.g., peptide fragments and fusion proteins) of DRT111. In the case of cell-free assays comprising a hydrophobic form of DRT111, it may be desirable to utilize a solubilizing agent such that the hydrophobic form of DRT111 is maintained in solution. Examples of such solubilizing agents include nonionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either DRT111 or its target molecule to facilitate separation of complexed from uncomplexed forms of one or both of the proteins, as well as to accommodate automation of the assay. Binding of a test compound to DRT111, or interaction of DRT111 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/DRT111 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or DRT111 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of DRT111 binding or activity determined using standard techniques.

Other techniques for immobilizing proteins on matrices can also be used in the screening assays of the invention. For example, either DRT111 or its target molecule can be immobilized utilizing conjugation of biotin and streptavidin. Biotinylated DRT111 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with DRT111 or target molecules but which do not interfere with binding of the DRT111 protein to its target molecule can be derivatized to the wells of the plate, and unbound target or DRT111 trapped in the wells by antibody conjugation. Methods for detecting such complexes, in addition to those described above for the GST-immobilized complexes, include immunodetection of complexes using antibodies reactive with the DRT111 or target molecule, as well as enzyme-linked assays which rely on detecting an enzymatic activity associated with the DRT111 or target molecule.

In another embodiment, modulators of DRT111 expression are identified in a method in which a cell is contacted with a candidate compound and the expression of DRT111 (mRNA or protein, or the copy number of the DRT111 gene) in the cell is determined. The level of expression of DRT111 in the presence of the candidate compound is compared to the level of expression of DRT111 in the absence of the candidate compound. The candidate compound can then be identified as a modulator of DRT111 expression based on this comparison. For example, when expression of DRT111 mRNA or protein is greater (statistically significantly greater) in the presence of the candidate compound than in its absence, the candidate compound is identified as a stimulator of DRT111 mRNA or protein expression. Alternatively, when expression of DRT111 mRNA or protein is less (statistically significantly less) in the presence of the candidate compound than in its absence, the candidate compound is identified as an inhibitor of DRT111 mRNA or protein expression. The level of DRT111 mRNA or protein expression in the cells, or the number of DRT111 gene copies per cell can be determined by methods described herein for detecting DRT111 genomic DNA, mRNA, or protein.

In yet another aspect of the invention, the DRT111 proteins can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and WO94/10300), to identify other proteins, which bind to or interact with DRT111 ("DRT111-binding proteins" or "DRT111-bp") and modulate DRT111 activity. Such DRT111-binding proteins are also likely to be involved in DNA damage repair or cellular resistance to chemotherapeutic drugs.

The two-hybrid system is based on the modular nature of most transcription factors, which consist of separable DNA-binding and activation domains. Briefly, the assay utilizes two different DNA constructs. In one construct, the gene that codes for DRT111 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an DRT111-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with DRT111.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene (or duplicates of the gene) on a chromosome. Accordingly, DRT111 nucleic acid molecules described herein or fragments thereof, can be used to map the location of DRT111 genes on a chromosome. The mapping of the DRT111 sequences to chromosomes is an important first step in correlating these sequences with genes associated with disease.

Briefly, DRT111 genes can be mapped to chromosomes by preparing PCR primers (preferably 15–25 bp in length) from the DRT111 sequences. Computer analysis of DRT111 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the DRT111 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the DRT111 sequences to design oligonucleotide primers, sublocalization can be achieved with panels of fragments from specific chromosomes. Other mapping strategies which can similarly be used to map a DRT111 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York, 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the DRT111 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The DRT111 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the DRT111 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The DRT111 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes.

Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from DRT111 sequences described herein is used to generate a unique identification database for an individual, those same reagents can later be used to identify tissue from that individual. Using the unique identification database, positive identification of the individual, living or dead, can be made from extremely small tissue samples.

3. Use of Partial DRT111 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the DRT111 sequences or portions thereof, e.g., fragments derived from the noncoding regions of SEQ ID NO:1 having a length of at least 20 or 30 bases.

The DRT111 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such DRT111 probes can be used to identify tissue by species and/or by organ type.

In a similar fashion, these reagents, e.g., DRT111 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining DRT111 protein and/or nucleic acid expression as well as DRT111 activity, in the context of a biological sample (e.g., blood, serum, cells, tissue) to thereby determine whether an individual is afflicted with a disease or disorder, or is at risk of developing a disorder, associated with aberrant DRT111 expression or activity. The invention also provides for prognostic (or predictive) assays for determining whether an individual is at risk of developing a disorder associated with DRT111 protein, nucleic acid expression or activity. For example, mutations in a DRT111 gene can be assayed in a biological sample. Such assays can be used for prognostic or predictive purpose to thereby prophylactically treat an individual prior to the onset of a disorder characterized by or associated with DRT111 protein, nucleic acid expression or activity.

Another aspect of the invention provides methods for determining DRT111 protein, nucleic acid expression or DRT111 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.) Yet another aspect of the invention pertains to monitoring the influence of agents (e.g., drugs or other compounds) on the expression or activity of DRT111 in clinical trials.

These and other agents are described in further detail in the following sections.

1. Diagnostic Assays

The invention provides a method of assessing expression, especially undesirable expression, of a cellular DRT111 gene. Undesirable (e.g., excessive) expression may indicate the presence, persistence or reappearance of drug-resistant (e.g., cyclophosphamide-resistant) tumor cells in an individual's tissue. More generally, aberrant expression may indicate the occurrence of a deleterious or disease-associated phenotype contributed to by DRT111.

An exemplary method for detecting the presence or absence of DRT111 in a biological sample involves obtaining a biological sample (preferably from a body site implicated in a possible diagnosis of diseased or malignant tissue) from a test subject and contacting the biological sample with a compound or an agent capable of detecting DRT111 protein or nucleic acid (e.g., mRNA, genomic DNA) that encodes DRT111 protein such that the presence of DRT111 is detected in the biological sample. The presence and/or relative abundance of DRT111 indicates aberrant or undesirable expression of a cellular DRT111 gene, and correlates with the occurrence in situ of cells having a drug-resistant phenotype.

A preferred agent for detecting DRT111 mRNA or genomic DNA is a labeled nucleic acid probe capable of hybridizing to DRT111 mRNA or genomic DNA. The nucleic acid probe can be, for example, a full-length DRT111 nucleic acid, such as the nucleic acid of SEQ ID NO: 1 or 3, or a portion thereof, such as an oligonucleotide of at least 15, 30, 50, 100, 250 or 500 nucleotides in length and sufficient to specifically hybridize under stringent conditions to DRT111 mRNA or genomic DNA. Other suitable probes for use in the diagnostic assays of the invention are described herein.

A preferred agent for detecting DRT111 protein is an antibody capable of binding to DRT111 protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect DRT111 mRNA, protein, or genomic DNA in a biological sample in vitro as well as in vivo. For example, in vitro techniques for detection of DRT111 mRNA include Northern hybridizations and in situ hybridizations. In vitro techniques for detection of DRT111 protein include enzyme linked immunosorbent assays (ELISAs), Western blots, immunoprecipitations and immunofluorescence. In vitro techniques for detection of DRT111 genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting DRT111 protein, mRNA, or genomic DNA, such that the presence of DRT111 protein, mRNA or genomic DNA is detected in the biological sample, and comparing the presence of DRT111 protein, mRNA or genomic DNA in the control sample with the presence of DRT111 protein, mRNA or genomic DNA in the test sample.

The invention also encompasses kits for detecting the presence of DRT111 in a biological sample (a test sample). Such kits can be used to determine if a subject is suffering from or is at increased risk of developing a disorder associated with aberrant expression of DRT111 (e.g., drug resistance). For example, the kit can comprise a labeled compound or agent capable of detecting DRT111 protein or mRNA in a biological sample and means for determining the amount of DRT111 in the sample (e.g., an anti-DRT111 antibody or an oligonucleotide probe which binds to DNA encoding DRT111, e.g., SEQ ID NO:1 or SEQ ID NO:3). Kits may also include instruction for observing that the tested subject is suffering from or is at risk of developing a disorder associated with aberrant expression of DRT111 if the amount of DRT111 protein or mRNA is above or below a normal level.

For antibody-based kits, the kit may comprise, for example: (1) a first antibody (e.g., attached to a solid support) which binds to DRT111 protein; and, optionally, (2) a second, different antibody which binds to DRT111 protein or the first antibody and is conjugated to a detectable agent.

For oligonucleotide-based kits, the kit may comprise, for example: (1) a oligonucleotide, e.g., a detectably labelled oligonucleotide, which hybridizes to a DRT111 nucleic acid sequence or (2) a pair of primers useful for amplifying a DRT111 nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of DRT111.

2. Prognostic Assays

The methods described herein can furthermore be utilized as diagnostic or prognostic assays to identify subjects having or at risk of developing a disease or disorder associated with aberrant DRT111 expression or activity. For example, the assays described herein, such as the preceding diagnostic assays or the following assays, can be utilized to identify a subject having or at risk of developing a disorder associated with DRT111 protein, nucleic acid expression or activity such as drug resistance of tumor cells. Alternatively, the prognostic assays can be utilized to identify a subject having or at risk for developing such a disease or disorder. Thus, the present invention provides a method in which a test sample is obtained from a subject and DRT111 protein or nucleic acid (e.g., mRNA, genomic DNA) is detected, wherein the presence or relative quantity of DRT111 protein or nucleic acid is diagnostic for a subject having or at risk of developing a disease or disorder associated with aberrant DRT111 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant DRT111 expression or activity. For example, such methods can be used to determine whether a subject can be effectively treated with a specific agent or class of agents (e.g., agents of a type which decrease DRT111 activity). Thus, the present invention provides methods for determining whether a subject can be effectively treated with an agent for a disorder associated with aberrant DRT111 expression or activity in which a test sample is obtained and DRT111 protein or nucleic acid is detected (e.g., wherein the presence or relative quantity of DRT111 protein or nucleic acid is diagnostic for a subject that can be administered the agent to treat a disorder associated with aberrant DRT111 expression or activity). In some embodiments, the foregoing methods provide information useful in prognostication, staging and management of malignancies (tumors) that are characterized by altered expression of DRT111 and thus by a drug-resistance phenotype. The information more specifically assists the clinician in designing chemotherapeutic or other treatment regimes to eradicate such malignancies from the body of an afflicted subject.

The methods of the invention can also be used to detect genetic lesions, mutations, or amplifications in a DRT111 gene, thereby determining if a subject with the lesioned gene is at risk for a disorder characterized by aberrant cell proliferation and/or differentiation. For example, genetic mutations, whether of germline or somatic origin, may indicate whether the process of developing drug resistance has been initiated or is likely to arise in the tested cells. In preferred embodiments, the methods include detecting, in a sample of cells from the subject, the presence or absence of a genetic lesion characterized by at least one of an alteration affecting the integrity of a gene encoding a DRT111-protein, the mis-expression of the DRT111 gene, or the amplification of a DRT111 gene. Preferably the sample of cells is obtained from a body tissue suspected of comprising transformed cells (e.g., cancer cells). Thus, the present method provides information relevant to diagnosis of the presence of a tumor.

Genetic lesions can be detected, for example, by ascertaining the existence of at least one of 1) a deletion of one or more nucleotides from a DRT111 gene; 2) an addition of one or more nucleotides to a DRT111 gene; 3) a substitution of one or more nucleotides of a DRT111 gene, 4) a chromosomal rearrangement of a DRT111 gene; 5) an alteration in the level of a messenger RNA transcript of a DRT111 gene, 6) aberrant modification of a DRT111 gene, such as of the methylation pattern of the genomic DNA, 7) the presence of a non-wild type splicing pattern of a messenger RNA transcript of a DRT111 gene, 8) a non-wild type level of a DRT111-protein, 9) allelic loss of a DRT111 gene, 10) amplification of a DRT111 gene, and 11) inappropriate post-translational modification of a DRT111-protein. As described herein, there are a large number of assay techniques known in the art which can be used for detecting lesions in a DRT111 gene. A preferred biological sample is a biopsy sample of tissue suspected of comprising transformed cells isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the DRT111-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a DRT111 gene under conditions such that hybridization and amplification of the DRT111-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a DRT111 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in DRT111 can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in DRT111 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the DRT111 gene and detect mutations by comparing the sequence of the sample DRT111 with the corresponding wild-type (control) sequence. Additionally, sequencing of the DNA flanking the DRT111 can be used to determine if the DRT111 gene has been amplified. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the DRT111 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type DRT111 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in DRT111 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a DRT111 sequence, e.g., a wild-type DRT111 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in DRT111 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet Anal Tech Appl* 9:73–79). Single-stranded DNA fragments of sample and control DRT111 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DRT111 gene.

Furthermore, any cell type or tissue, preferably biopsy samples of tissue comprising or suspected of comprising transformed cells, in which DRT111 is expressed may be utilized in the prognostic assays described herein.

3. Pharmacogenomics

Agents, or modulators which have a stimulatory or inhibitory effect on DRT111 activity (e.g., DRT111 gene expression) as identified by a screening assay described herein can be administered to individuals to treat (prophylactically or therapeutically) disorders (e.g., drug-resistance) associated with aberrant DRT111 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of DRT111 protein, expression of DRT111 nucleic acid, or mutation content of DRT111 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of DRT111 protein, expression of DRT111 nucleic acid, or mutation content of DRT111 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a DRT111 modulator, such as a modulator identified by one of the exemplary screening assays described herein.

4. Monitoring of Effects During Clinical Trials

Monitoring the influence of agents (e.g., drugs, compounds) on the expression or activity of DRT111 (e.g., the ability to modulate the drug-resistant phenotype of a cell) can be applied not only in basic drug screening, but also in clinical trials. For example, the effectiveness of an agent determined by a screening assay as described herein to increase DRT111 gene expression, protein levels, or upregulate DRT111 activity, can be monitored in clinical trails of subjects exhibiting decreased DRT111 gene expression, protein levels, or downregulated DRT111 activity. Alternatively, the effectiveness of an agent determined by a screening assay to decrease DRT111 gene expression, protein levels, or downregulated DRT111 activity, can be monitored in clinical trails of subjects exhibiting increased DRT111 gene expression, protein levels, or upregulated DRT111 activity. In such clinical trials, the expression or activity of DRT111 and, preferably, other genes that have been implicated in, for example, a cellular proliferation disorder, can be used as a "read out" or markers of the drug resistance of a particular cell.

For example, and not by way of limitation, genes, including DRT111, that are modulated in cells by treatment with an agent (e.g., compound, drug or small molecule) which modulates DRT111 activity (e.g., identified in a screening assay as described herein) can be identified. Thus, to study the effect of agents on cellular proliferation disorders, for example, in a clinical trial, cells can be isolated and RNA prepared and analyzed for the levels of expression of DRT111 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of DRT111 or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a DRT111 protein, mRNA, or genomic DNA in the preadministration sample; (iii) obtaining one or more post-administration samples from the subject; (iv) detecting the level of expression or activity of the DRT111 protein, mRNA, or genomic DNA in the post-administration samples; (v) comparing the level of expression or activity of the DRT111 protein, mRNA, or genomic DNA in the pre-administration sample with the DRT111 protein, mRNA, or genomic DNA in the post administration sample or samples; and (vi) altering the administration of the agent to the subject accordingly. For example, increased administration of the agent may be desirable to increase the expression or activity of DRT111 to higher levels than detected, i.e., to increase the effectiveness of the agent. Alternatively, decreased administration of the agent may be desirable to decrease expression or activity of DRT111 to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant DRT111 expression or activity. Such disorders include DNA repair disorders (e.g., mutations associated with aberrant DNA repair) and cellular resistance to chemotherapeutic drugs.

1. Prophylactic Methods

In one aspect, the invention provides a method for preventing in a subject, a disease or condition associated with an aberrant DRT111 expression or activity (e.g., the development of drug resistance), by administering to the subject an agent which modulates DRT111 expression or at least one DRT111 activity. Subjects at risk for a condition which is caused or contributed to by aberrant DRT111 expression or activity can be identified by, for example, any or a combination of diagnostic or prognostic assays as described herein. Administration of a prophylactic agent can occur prior to the manifestation of symptoms characteristic of the DRT111 aberrancy, such that a disease or disorder is prevented or, alternatively, delayed in its progression. For example, administration of a prophylatic agent to a cancer patient may prevent or delay the development of drug resistance in the patient's cancer cells. Depending on the type of DRT111 aberrancy, for example, a DRT111 agonist or DRT111 antagonist agent can be used for treating the subject. The appropriate agent can be determined based on screening assays described herein.

2. Therapeutic Methods

Another aspect of the invention pertains to methods of modulating DRT111 expression or activity for therapeutic purposes. For example, the effectiveness of chemotherapy is "potentiated" (enhanced) by restoring or improving vulnerability of the transformed cells to the cytotoxic effects of a chemotherapeutic drug that otherwise would be less effective by reducing the expression of DRT111 in the cells. The modulatory method of the invention involves contacting a cell with an agent that modulates one or more of the activities of DRT111 protein activity associated with the cell. An agent that modulates DRT111 protein activity can be an agent as described herein, such as a nucleic acid or a protein, a naturally-occurring cognate ligand of a DRT111 protein, a peptide, a DRT111 peptidomimetic, or other small molecule. In one embodiment, the agent stimulates one or more of the biological activities of DRT111 protein. Examples of such stimulatory agents include active DRT111 protein and a nucleic acid molecule encoding DRT111 that has been introduced into the cell. In another embodiment, the agent inhibits one or more of the biological activities of DRT111 protein. Examples of such inhibitory agents include antisense DRT111 nucleic acid molecules and anti-DRT111 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a DRT111 protein or nucleic acid molecule. In one embodiment, the method involves administering an agent (e.g., an agent identified by a screening assay described herein), or combination of agents that modulates (e.g., upregulates or downregulates) DRT111 expression or activity. In another embodiment, the method involves administering a DRT111 protein or nucleic acid molecule as therapy to compensate for reduced or aberrant DRT111 expression or activity.

For example, in one embodiment, the method involves administering the desired drug (e.g., cyclophosphamide) to an individual afflicted with a drug-resistant cell population (a tumor, e.g., a carcinoma, sarcoma, leukemia, lymphoma, or lymphosarcoma), and coadministering an inhibitor of DRT111 expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an DRT111 antisense oligonucleotide in combination with one or more other antisense oligonucleotides) can be administered to the individual sufficiently in advance of administration of the chemotherapeutic drug to allow the antisense composition to permeate the individual's tissues, especially tissue comprising the transformed cells to be eradicated; to be internalized by transformed cells; and to disrupt DRT111 gene expression and/or protein production.

Stimulation of DRT111 activity is desirable in situations in which DRT111 is abnormally downregulated and/or in which increased DRT111 activity is likely to have a beneficial effect. Conversely, inhibition of DRT111 activity is desirable in situations in which DRT111 is abnormally upregulated and/or in which decreased DRT111 activity is likely to have a beneficial effect.

This invention is further illustrated by the following examples which should not be construed as limiting. The contents of all references, patents and published patent applications cited throughout this application are hereby incorporated by reference.

EXAMPLES

Example 1
Isolation and Characterization of a Human DRT111 cDNA

In order to identify genes that are more highly expressed in EMT-6 CTX cells than in EMT-6 cells, a subtraction library (Diacheno et al., *Proc. Nat'l Acad. Sci. USA* 93:6025–6030 (1996)) was prepared using EMT-6 cells, a murine tumor cell line, and EMT-6 CTX cells (cyclophosphamide resistant tumor cells derived from the EMT-6 tumor cell line; Teicher et al., *Science* 247:1457–1461, 1990). A number of the library clones were sequenced. A BLAST search using the predicted amino acid sequences of these clones led to the identification of a clone (comvc007a03) encoding a protein having some homology to *Arabidopsis thaliana* DRT111. Previous studies suggest that *A. thaliana* DRT111 plays a role in DNA damage repair. Pang et al., *Nucleic Acids Research* 21:1647–1653, 1993.

A nomenclature search (using "DRT111") of the NCBI Unigene database led to the identification of several human expressed sequence tags (ESTs). The nucleic acid sequence of each of these ESTs was obtained from The Institute for Genomics Research (Rockville, Md.). These sequences were aligned with the above murine clone (comvc007a03). The EST (IMAGE CLONE #1046783) with the highest sequence identity to the murine clone was then used to probe a human prostate fibroblast ziplock library. This led to the isolation of a full length clone corresponding to human DRT111 (SEQ ID NO:1).

Example 2
Characterization of DRT111 Proteins

In this example, the predicted amino acid sequence of human DRT111 protein was compared to amino acid sequences of known proteins and various motifs were identified. In addition, the molecular weight of the human DRT111 proteins was predicted.

The human DRT111 cDNA isolated as described above (FIG. 1; SEQ ID NO:1) encodes a 401 amino acid protein (FIG. 1; SEQ ID NO:2).

As shown in FIGS. 2A–2B, the amino acid sequence of human DRT111 protein (SEQ ID NO:2) has high homology to the amino acid sequences of *A. thaliana* DRT111 protein and murine DRT111 protein (SEQ ID NO:7). DRT111 has a predicted MW of 44,960 Da, not including post-translational modifications.

Example 3
Preparation of DRT111 Proteins

Recombinant DRT111 can be produced in a variety of expression systems. For example, the mature DRT111 peptide can be expressed as a recombinant glutathione-S-transferase (GST) fusion protein in *E. coli* and the fusion protein can be isolated and characterized. Specifically, as described above, DRT111 can be fused to GST and this fusion protein can be expressed in *E. coli* strain PEB199. As DRT111 is predicted to be 44,960 Da and GST is predicted to be 26,000 Da, the fusion protein is predicted to be 70,960 Da in molecular weight. Expression of the GST-DRT111 fusion protein in PEB199 can be induced with IPTG. The recombinant fusion protein can be purified from crude bacterial lysates of the induced PEB199 strain by affinity chromatography on glutathione beads. Using polyacrylamide gel electrophoretic analysis of the proteins purified from the bacterial lysates, the resultant fusion protein should be 70,960 Da in size.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a nucleotide sequence which encodes a polypeptide comprising at least 150 contiguous amino acid residues of SEQ ID NO:2.

2. The nucleic acid molecule of claim 1 which comprises a nucleotide sequence which encodes a polypeptide comprising at least 300 contiguous amino acid residues of SEQ ID NO:2.

3. The nucleic acid molecule of claim 2 which comprises a nucleotide sequence which encodes a polypeptide comprising at least 400 contiguous amino acid residues of SEQ ID NO:2.

4. An isolated nucleic acid molecule comprising a nucleotide sequence which encodes a polypeptide comprising the amino acid sequence of SEQ ID NO:2.

5. An isolated nucleic acid molecule comprising the nucleotide sequence of SEQ ID NO:1.

6. An isolated nucleic acid molecule comprising the nucleotide sequence of the cDNA insert of the plasmid deposited with ATCC as Accession Number 209937.

* * * * *

SEQUENCE LISTING

<160> NUMBER OF SEQ ID NOS: 9

<210> SEQ ID NO 1
<211> LENGTH: 1695
<212> TYPE: DNA

<213> ORGANISM: Homo sapiens

<400> SEQUENCE: 1

```
gtcgacccac gcgtccgggg tgggcgccgc cgaggcctcc tgccgctggc gggtttccgc     60
ggagtgccgc ccggctccgc tctgccgccg gcgcggctca tgggcagagt cggccgggcg    120
ggccggcatt aaactgaaga aaagatgtcc ctgtacgatg acctaggagt ggagaccagt    180
gactcaaaaa cagaaggctg gtccaaaaac ttcaaacttc tgcagtctca gcttcaggtg    240
aagaaggcag ctctcactca ggcaaagagc caaggacga aacaaagtac agtcctcgcc     300
ccagtcattg acctgaagcg aggtggctcc tcagatgacc ggcaaattgt ggacactcca    360
ccgcatgtag cagctgggct gaaggatcct gttcccagtg ggttttctgc aggggaagtt    420
ctgattccct tagctgacga atatgaccct atgtttccta atgattatga aaagtagtg     480
aagcgccaaa gagaggaacg acagagacag cgggagctgg aaagacaaaa ggaaatagaa    540
gaaagggaaa aaggcgtaa agacagacat gaagcaagtg ggtttgcaag agaccagat      600
ccagattctg atgaagatga agattatgag cgagagagga ggaaaagaag tatgggcgga    660
gctgccattg ccccacccac ttctctggta gagaaagaca aagagttacc ccgagatttt    720
ccttatgaag aggactcaag acctcgatca cagtcttcca aagcagccat tcctccccca    780
gtgtacgagg aacaagacag accgagatct ccaaccggac ctagcaactc cttcctcgct    840
aacatggggg gcacggtggc gcacaagatc atgcagaagt acggcttccg ggagggccag    900
ggtctgggga agcatgagca gggcctgagc actgccttgt cagtggagaa gaccagcaag    960
cgtggcggca agatcatcgt gggcgacgcc acagagaaag atgcatccaa gaagtcagat   1020
tcaaaatccg ctgactgaaa tacttaagtg tcctactaaa gtggtcttac taaggaacat   1080
ggttggtgcg ggagaggtgg atgaagactt ggaagttgaa accaaggaag aatgtgaaaa   1140
atatggcaaa gttggaaaat gtgtgatatt tgaaattcct ggtgcccctg atgatgaagc   1200
agtacggata ttttagaat ttgagagagt tgaatcagca attaaagcgg ttgttgactt    1260
gaatgggagg tattttggtg gacgggtggt aaaagcatgt ttctacaatt tggacaaatt   1320
cagggtcttg gatttggcag aacaagtttg attttaagaa ctagagcacg agtcatctcc   1380
ggtgatcctt aaatgaactg caggctgaga aagaaggaa aaaggtcaca gcctccatgg    1440
ctgttgcata ccaagactct tggaaggact tctaagatat atgttgattg atcccttttt   1500
tattttgtgg tttttttaata tagtataaaa atccttttaa aaaacaaca atctgtgtgc    1560
ctctctggtt gtttctcttt tttattatta ctcctgagtt gatgacattt tttgttagat   1620
ttcatggtaa ttctcaagtg cttcaatgat gcagcatttc ttgcactaaa aaaaaaaaa    1680
aaaaagggcg gccgc                                                    1695
```

<210> SEQ ID NO 2
<211> LENGTH: 401
<212> TYPE: PRT
<213> ORGANISM: Homo sapiens

<400> SEQUENCE: 2

Met Ser Leu Tyr Asp Asp Leu Gly Val Glu Thr Ser Asp Ser Lys Thr
 1               5                  10                  15

Glu Gly Trp Ser Lys Asn Phe Lys Leu Leu Gln Ser Gln Leu Gln Val
            20                  25                  30

Lys Lys Ala Ala Leu Thr Gln Ala Lys Ser Gln Arg Thr Lys Gln Ser
        35                  40                  45

-continued

| | | | | | | | | | | | |
|---|---|---|---|---|---|---|---|---|---|---|---|
|Thr|Val|Leu|Ala|Pro|Val|Ile|Asp|Leu|Lys|Arg|Gly|Gly|Ser|Ser|Asp|
| |50| | | |55| | | |60| | | | | | |

Thr Val Leu Ala Pro Val Ile Asp Leu Lys Arg Gly Gly Ser Ser Asp
        50                  55                  60

Asp Arg Gln Ile Val Asp Thr Pro Pro His Val Ala Ala Gly Leu Lys
 65                  70                  75                  80

Asp Pro Val Pro Ser Gly Phe Ser Ala Gly Glu Val Leu Ile Pro Leu
                 85                  90                  95

Ala Asp Glu Tyr Asp Pro Met Phe Pro Asn Asp Tyr Glu Lys Val Val
            100                 105                 110

Lys Arg Gln Arg Glu Glu Arg Gln Arg Gln Arg Glu Leu Glu Arg Gln
        115                 120                 125

Lys Glu Ile Glu Glu Arg Glu Lys Arg Arg Lys Asp Arg His Glu Ala
        130                 135                 140

Ser Gly Phe Ala Arg Arg Pro Asp Pro Asp Ser Asp Glu Asp Glu Asp
145                 150                 155                 160

Tyr Glu Arg Glu Arg Arg Lys Arg Ser Met Gly Gly Ala Ala Ile Ala
                165                 170                 175

Pro Pro Thr Ser Leu Val Glu Lys Asp Lys Glu Leu Pro Arg Asp Phe
            180                 185                 190

Pro Tyr Glu Glu Asp Ser Arg Pro Arg Ser Gln Ser Ser Lys Ala Ala
        195                 200                 205

Ile Pro Pro Pro Val Tyr Glu Glu Gln Asp Arg Pro Arg Ser Pro Thr
210                 215                 220

Gly Pro Ser Asn Ser Phe Leu Ala Asn Met Gly Gly Thr Val Ala His
225                 230                 235                 240

Lys Ile Met Gln Lys Tyr Gly Phe Arg Glu Gly Gln Gly Leu Gly Lys
                245                 250                 255

His Glu Gln Gly Leu Ser Thr Ala Leu Ser Val Glu Lys Thr Ser Lys
            260                 265                 270

Arg Gly Gly Lys Ile Ile Val Gly Asp Ala Thr Glu Lys Asp Ala Ser
        275                 280                 285

Lys Lys Ser Asp Ser Asn Pro Leu Thr Glu Ile Leu Lys Cys Pro Thr
290                 295                 300

Lys Val Val Leu Leu Arg Asn Met Val Gly Ala Gly Glu Val Asp Glu
305                 310                 315                 320

Asp Leu Glu Val Glu Thr Lys Glu Glu Cys Glu Lys Tyr Gly Lys Val
                325                 330                 335

Gly Lys Cys Val Ile Phe Glu Ile Pro Gly Ala Pro Asp Asp Glu Ala
            340                 345                 350

Val Arg Ile Phe Leu Glu Phe Glu Arg Val Glu Ser Ala Ile Lys Ala
        355                 360                 365

Val Val Asp Leu Asn Gly Arg Tyr Phe Gly Gly Arg Val Val Lys Ala
370                 375                 380

Cys Phe Tyr Asn Leu Asp Lys Phe Arg Val Leu Asp Leu Ala Glu Gln
385                 390                 395                 400

Val

<210> SEQ ID NO 3
<211> LENGTH: 1204
<212> TYPE: DNA
<213> ORGANISM: Homo sapiens

<400> SEQUENCE: 3
atgtccctgt acgatgacct aggagtggag accagtgact caaaaacaga aggctggtcc      60
aaaaacttca aacttctgca gtctcagctt caggtgaaga aggcagctct cactcaggca     120

-continued

```
aagagccaaa ggacgaaaca aagtacagtc ctcgccccag tcattgacct gaagcgaggt    180
ggctcctcag atgaccggca aattgtggac actccaccgc atgtagcagc tgggctgaag    240
gatcctgttc ccagtgggtt ttctgcaggg aagttctga ttcccttagc tgacgaatat    300
gaccctatgt ttcctaatga ttatgagaaa gtagtgaagc gccaaagaga ggaacgacag    360
agacagcggg agctggaaag acaaaaggaa atagaagaaa gggaaaaaag gcgtaaagac    420
agacatgaag caagtggggtt tgcaaggaga ccagatccag attctgatga agatgaagat    480
tatgagcgag agaggaggaa aagaagtatg ggcggagctg ccattgcccc acccacttct    540
ctggtagaga aagacaaaga gttaccccga gattttcctt atgaagagga ctcaagacct    600
cgatcacagt cttccaaagc agccattcct cccccagtgt acgaggaaca agacagaccg    660
agatctccaa ccggacctag caactccttc ctcgctaaca tggggggcac ggtggcgcac    720
aagatcatgc agaagtacgg cttccgggag gccagggtc tggggaagca tgagcagggc    780
ctgagcactg ccttgtcagt ggagaagacc agcaagcgtg gcggcaagat catcgtgggc    840
gacgccacag agaagatgc atccaagaag tcagattcaa aatccgctga ctgaaatact    900
taagtgtcct actaaagtgg tcttactaag gaacatggtt ggtgcgggag aggtggatga    960
agacttggaa gttgaaacca aggaagaatg tgaaaaatat ggcaaagttg gaaaatgtgt   1020
gatatttgaa attcctggtg cccctgatga tgaagcagta cggatatttt tagaatttga   1080
gagagttgaa tcagcaatta aagcggttgt tgacttgaat gggaggtatt ttggtggacg   1140
ggtggtaaaa gcatgtttct acaatttgga caaattcagg gtcttggatt tggcagaaca   1200
agtt                                                                1204
```

<210> SEQ ID NO 4
<211> LENGTH: 30
<212> TYPE: DNA
<213> ORGANISM: Artificial Sequence
<220> FEATURE:
<223> OTHER INFORMATION: primer_bind

<400> SEQUENCE: 4

```
aaactgaaga aaagatgtcc ctgtacgatg                                      30
```

<210> SEQ ID NO 5
<211> LENGTH: 25
<212> TYPE: DNA
<213> ORGANISM: Artificial Sequence
<220> FEATURE:
<223> OTHER INFORMATION: primer_bind

<400> SEQUENCE: 5

```
gaaaagatgt ccctgtacga tgacc                                           25
```

<210> SEQ ID NO 6
<211> LENGTH: 1542
<212> TYPE: DNA
<213> ORGANISM: Mus musculus
<220> FEATURE:
<221> NAME/KEY: misc_feature
<222> LOCATION: (1)...(1542)
<223> OTHER INFORMATION: n = A,T,C or G

<400> SEQUENCE: 6

```
ctacaccccg cgtacgcgga cgcgtggggc gctgcggcgg actccggcgg tgggcgggct     60
tccgcgcagg gcggccgggc tccgcgctgc cgccgccgtg gcccatgggc acaatcgtct    120
```

-continued

```
cggaaggccg gcattaaacc aaaaagatgt ccctatatga tgacctggga gtggagacca      180
gtgactcaaa aactgaaggc tggtccaaaa acttcaagct cctgcagtcc cagctccagg      240
tgaagaaggc ggcgctcact caggccaaga gccaaaggac caagcaaagt acagtgcttg      300
ctccggtcat cgacctaaag cgaggcggct cctcagatga ccggcagatt gcagacacac      360
cacctcacgt ggcagctggg ctgaaggacc ctgtgcccag tgggttttct gcaggggaag      420
ttctgatccc cttagctgat gaatatgacc ctatgttccc caatgactat gagaaagtgg      480
tgaagcgcca gagagaagag cggcagaggc agcgggagct ggaaagacag aaggaaatag      540
aggaaagaga aaagaggcgt aaagacagac acgaagccag tgggttttca agacgaccag      600
accctgattc tgatgaggat gaagattatg agcgagagcg nnggaaaaga agtatgggag      660
gagctgccat cgccccaccg acgtctcttg tagagaaaga caaagagtta cccgcgatt       720 ttccttatga agaggactca agaccgagat cacagtcttc caaagctgct attcctcccc      780
ccgtgtatga ggagccggac agaccaagat ctccaacagg ccccagcaac tccttccttg      840
ctaacatggg tggcacagtg gctcataaga ttatgcagaa gtatggcttc cgggaaggtc      900
agggactggg gaaacacgag caagggctga gtactgcatt gtctgtggag aagaccagca      960
agcgtggcgg caagatcatt gtgggggatg cgacagagaa nggcgaggct caggatgcat     1020
ccaaaaagtc ggattcaaat ccattaactg aaattcttaa gtgccctact aaagtggtct     1080
tgctgaggaa catggttggt gcaggagagg tcgatgaaga cttggaagtt gaaaccaagg     1140
aagaatgtga aaaatatggc aaagttggga atgtgtgat atttgagatt cctggtgccc      1200
ctgatgatga agcagtacgg atatttttag aatttgagag agtcnaatca gcaattaaag     1260
ctgtggtgga tctgaatggg angtattttg gtggacgggt ggtaaaagca tgtttctaca     1320
atttggataa attcaggggtc ttggatctag cagacaagtt tgattgtaac ttaaagtcac     1380
ctccttgatc cttacatgag ctacagactg aacaatgaca caggcatggc tgttgtgtca     1440
tggctggtgg acctgaaact cttggatggc ttctaaatat tgttgaggat cttttttata     1500
tgtggttctt atatagataa atctttaaat caaaaaaaaa aa                        1542
```

<210> SEQ ID NO 7
<211> LENGTH: 413
<212> TYPE: PRT
<213> ORGANISM: Mus musculus
<220> FEATURE:
<221> NAME/KEY: VARIANT
<222> LOCATION: (1)...(413)
<223> OTHER INFORMATION: Xaa = Any Amino Acid

<400> SEQUENCE: 7

Met Ser Leu Tyr Asp Asp Leu Gly Val Glu Thr Ser Asp Ser Lys Thr
 1               5                  10                  15

Glu Gly Trp Ser Lys Asn Phe Lys Leu Leu Gln Ser Gln Leu Gln Val
            20                  25                  30

Lys Lys Ala Ala Leu Thr Gln Ala Lys Ser Gln Arg Thr Lys Gln Ser
        35                  40                  45

Thr Val Leu Ala Pro Val Ile Asp Leu Lys Arg Gly Gly Ser Ser Asp
    50                  55                  60

Asp Arg Gln Ile Ala Asp Thr Pro Pro His Val Ala Ala Gly Leu Lys
65                  70                  75                  80

Asp Pro Val Pro Ser Gly Phe Ser Ala Gly Glu Val Leu Ile Pro Leu
                85                  90                  95

Ala Asp Glu Tyr Asp Pro Met Phe Pro Asn Asp Tyr Glu Lys Val Val

-continued

```
                100                 105                 110
Lys Arg Gln Arg Glu Arg Gln Arg Gln Arg Glu Leu Glu Arg Gln
            115                 120                 125

Lys Glu Ile Glu Glu Arg Glu Lys Arg Arg Lys Asp Arg His Glu Ala
130                 135                 140

Ser Gly Phe Ser Arg Arg Pro Asp Pro Asp Ser Asp Glu Asp Glu Asp
145                 150                 155                 160

Tyr Glu Arg Glu Arg Xaa Lys Arg Ser Met Gly Gly Ala Ala Ile Ala
                165                 170                 175

Pro Pro Thr Ser Leu Val Glu Lys Asp Lys Glu Leu Pro Arg Asp Phe
            180                 185                 190

Pro Tyr Glu Glu Asp Ser Arg Pro Arg Ser Gln Ser Ser Lys Ala Ala
            195                 200                 205

Ile Pro Pro Pro Val Tyr Glu Glu Pro Asp Arg Pro Arg Ser Pro Thr
210                 215                 220

Gly Pro Ser Asn Ser Phe Leu Ala Asn Met Gly Gly Thr Val Ala His
225                 230                 235                 240

Lys Ile Met Gln Lys Tyr Gly Phe Arg Glu Gly Gln Gly Leu Gly Lys
                245                 250                 255

His Glu Gln Gly Leu Ser Thr Ala Leu Ser Val Glu Lys Thr Ser Lys
            260                 265                 270

Arg Gly Gly Lys Ile Ile Val Gly Asp Ala Thr Glu Xaa Gly Glu Ala
            275                 280                 285

Gln Asp Ala Ser Lys Lys Ser Asp Ser Asn Pro Leu Thr Glu Ile Leu
    290                 295                 300

Lys Cys Pro Thr Lys Val Val Leu Leu Arg Asn Met Val Gly Ala Gly
305                 310                 315                 320

Glu Val Asp Glu Asp Leu Glu Val Glu Thr Lys Glu Glu Cys Glu Lys
                325                 330                 335

Tyr Gly Lys Val Gly Lys Cys Val Ile Phe Glu Ile Pro Gly Ala Pro
            340                 345                 350

Asp Asp Glu Ala Val Arg Ile Phe Leu Glu Phe Glu Arg Val Xaa Ser
            355                 360                 365

Ala Ile Lys Ala Val Val Asp Leu Asn Gly Xaa Tyr Phe Gly Gly Arg
    370                 375                 380

Val Val Lys Ala Cys Phe Tyr Asn Leu Asp Lys Phe Arg Val Leu Asp
385                 390                 395                 400

Leu Ala Asp Lys Phe Asp Cys Asn Leu Lys Ser Pro Pro
                405                 410
```

<210> SEQ ID NO 8
<211> LENGTH: 383
<212> TYPE: PRT
<213> ORGANISM: Arabidopsis thaliana

<400> SEQUENCE: 8

```
Met Leu Gly Gly Leu Tyr Gly Asp Leu Pro Pro Thr Asp Asp Glu
1               5                   10                  15

Lys Pro Ser Gly Asn Ser Ser Val Trp Ser Arg Ser Thr Lys Met
                20                  25                  30

Ala Pro Pro Thr Leu Arg Lys Pro Ala Phe Ala Pro Pro Gln Thr
            35                  40                  45

Ile Leu Arg Pro Leu Asn Lys Pro Lys Pro Ile Val Ser Ala Pro Tyr
    50                  55                  60
```

```
Lys Pro Pro Asn Ser Ser Gln Ser Val Leu Ile Pro Ala Asn Glu
 65                  70                  75                  80

Ser Ala Pro Ser His Gln Pro Ala Leu Val Gly Val Thr Ser Ser Val
             85                  90                  95

Ile Glu Glu Tyr Asp Pro Ala Arg Pro Asn Asp Tyr Glu Glu Tyr Lys
            100                 105                 110

Arg Glu Lys Lys Arg Lys Ala Thr Glu Ala Glu Met Lys Arg Glu Met
        115                 120                 125

Asp Lys Arg Arg Gln Val Tyr Pro Glu Arg Asp Met Arg Glu Arg Glu
130                 135                 140

Glu Arg Glu Arg Arg Glu Arg Glu Ile Thr Val Ile Leu Ser Val Asp
145                 150                 155                 160

Ile Ser Gly Glu Glu Arg Gly Arg Asp Pro Ala Arg Val Val Val Glu
                165                 170                 175

Val Leu Gly Arg Glu Asp Pro Arg Leu Leu Pro Gly Asn Val Asp Gly
            180                 185                 190

Phe Ser Ile Gly Lys Ser Lys Pro Ser Gly Leu Gly Val Gly Ala Gly
        195                 200                 205

Gly Gln Met Thr Pro Ala Gln Arg Met Met Pro Lys Met Gly Trp Lys
210                 215                 220

Gln Gly Gln Gly Leu Gly Lys Ser Glu Gln Gly Ile Pro Thr Pro Leu
225                 230                 235                 240

Met Ala Lys Lys Thr Asp Arg Arg Ala Gly Val Ile Val Asn Ala Ser
                245                 250                 255

Glu Asn Lys Ser Ser Ala Glu Lys Lys Val Val Lys Ser Val Asn
            260                 265                 270

Ile Asn Gly Glu Pro Thr Arg Val Leu Leu Arg Asn Met Val Gly
        275                 280                 285

Pro Gly Gln Val Asp Asp Glu Leu Glu Asp Glu Val Gly Gly Glu Cys
            290                 295                 300

Ala Lys Tyr Gly Thr Val Thr Arg Val Leu Ile Phe Glu Ile Thr Glu
305                 310                 315                 320

Pro Asn Phe Pro Val His Glu Ala Val Arg Ile Phe Val Gln Phe Ser
                325                 330                 335

Arg Pro Glu Glu Thr Thr Lys Ala Leu Val Asp Leu Asp Gly Arg Tyr
            340                 345                 350

Phe Gly Gly Arg Thr Val Arg Ala Thr Phe Tyr Asp Glu Glu Lys Phe
        355                 360                 365

Ser Lys Asn Glu Leu Ala Pro Val Pro Gly Glu Ile Pro Gly Tyr
370                 375                 380
```

<210> SEQ ID NO 9
<211> LENGTH: 413
<212> TYPE: PRT
<213> ORGANISM: Artificial Sequence
<220> FEATURE:
<221> NAME/KEY: VARIANT
<222> LOCATION: (1)...(413)
<223> OTHER INFORMATION: Xaa = Any Amino Acid
<223> OTHER INFORMATION: consensus sequence

<400> SEQUENCE: 9

```
Met Ser Leu Tyr Asp Asp Leu Gly Val Glu Thr Ser Asp Ser Lys Thr
 1               5                  10                  15

Glu Gly Trp Ser Lys Asn Phe Lys Leu Leu Gln Ser Gln Leu Gln Val
            20                  25                  30
```

-continued

```
Lys Lys Ala Ala Leu Thr Gln Ala Lys Ser Gln Arg Thr Lys Gln Ser
            35                  40                  45

Thr Val Leu Ala Pro Val Ile Asp Leu Lys Arg Gly Gly Ser Ser Asp
        50                  55                  60

Asp Arg Gln Ile Xaa Asp Thr Pro Pro His Val Ala Ala Gly Leu Lys
 65              70                  75                      80

Asp Pro Val Pro Ser Gly Phe Ser Ala Gly Glu Val Leu Ile Pro Leu
                85                  90                  95

Ala Asp Glu Tyr Asp Pro Met Phe Pro Asn Asp Tyr Glu Lys Val Val
            100                 105                 110

Lys Arg Gln Arg Glu Glu Arg Gln Arg Gln Arg Glu Leu Glu Arg Gln
            115                 120                 125

Lys Glu Ile Glu Glu Arg Glu Lys Arg Arg Lys Asp Arg His Glu Ala
            130                 135                 140

Ser Gly Phe Xaa Arg Arg Pro Asp Pro Asp Ser Asp Glu Asp Glu Asp
145                 150                 155                 160

Tyr Glu Arg Glu Arg Arg Lys Arg Ser Met Gly Gly Ala Ala Ile Ala
                165                 170                 175

Pro Pro Thr Ser Leu Val Glu Lys Asp Lys Glu Leu Pro Arg Asp Phe
            180                 185                 190

Pro Tyr Glu Glu Asp Ser Arg Pro Arg Ser Gln Ser Ser Lys Ala Ala
            195                 200                 205

Ile Pro Pro Pro Val Tyr Glu Glu Xaa Asp Arg Pro Arg Ser Pro Thr
            210                 215                 220

Gly Pro Ser Asn Ser Phe Leu Ala Asn Met Gly Gly Thr Val Ala His
225                 230                 235                 240

Lys Ile Met Gln Lys Tyr Gly Phe Arg Glu Gly Gln Gly Leu Gly Lys
                245                 250                 255

His Glu Gln Gly Leu Ser Thr Ala Leu Ser Val Glu Lys Thr Ser Lys
                260                 265                 270

Arg Gly Gly Lys Ile Ile Val Gly Asp Ala Thr Glu Xaa Xaa Xaa Ala
            275                 280                 285

Xaa Asp Ala Ser Lys Lys Ser Asp Ser Asn Pro Leu Thr Glu Ile Leu
290                 295                 300

Lys Cys Pro Thr Lys Val Val Leu Leu Arg Asn Met Val Gly Ala Gly
305                 310                 315                 320

Glu Val Asp Glu Asp Leu Glu Val Glu Thr Lys Glu Glu Cys Glu Lys
                325                 330                 335

Tyr Gly Lys Val Gly Lys Cys Val Ile Phe Glu Ile Pro Gly Ala Pro
                340                 345                 350

Asp Asp Glu Ala Val Arg Ile Phe Leu Glu Phe Glu Arg Val Glu Ser
            355                 360                 365

Ala Ile Lys Ala Val Val Asp Leu Asn Gly Arg Tyr Phe Gly Gly Arg
            370                 375                 380

Val Val Lys Ala Cys Phe Tyr Asn Leu Asp Lys Phe Arg Val Leu Asp
385                 390                 395                 400

Leu Ala Xaa Xaa Xaa Xaa Xaa Xaa Xaa Xaa Pro Xaa
                405                 410
```